United States Patent
Kim et al.

(10) Patent No.: US 10,485,512 B2
(45) Date of Patent: Nov. 26, 2019

(54) ULTRASONIC DIAGNOSTIC APPARATUS AND CONTROL METHOD THEREOF

(71) Applicant: SAMSUNG ELECTRONICS CO., LTD., Suwon-si (KR)

(72) Inventors: Baehyung Kim, Yongin-si (KR); Youngil Kim, Suwon-si (KR); Jong Keun Song, Yongin-si (KR); Seungheun Lee, Seongnam-si (KR); Kyungil Cho, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 818 days.

(21) Appl. No.: 14/568,342

(22) Filed: Dec. 12, 2014

(65) Prior Publication Data

US 2015/0164473 A1     Jun. 18, 2015

(30) Foreign Application Priority Data

Dec. 12, 2013 (KR) .................. 10-2013-0154977

(51) Int. Cl.
| | |
|---|---|
| *A61B 8/00* | (2006.01) |
| *G01S 15/89* | (2006.01) |
| *G01S 7/52* | (2006.01) |
| *G10K 11/34* | (2006.01) |

(Continued)

(52) U.S. Cl.
CPC ........... *A61B 8/4494* (2013.01); *A61B 8/145* (2013.01); *A61B 8/4483* (2013.01); *A61B 8/483* (2013.01); *A61B 8/54* (2013.01); *G01S 7/52047* (2013.01); *G01S 7/52085* (2013.01); *G01S 15/8925* (2013.01); *G01S 15/8927* (2013.01); *G01S 15/8993* (2013.01); *G01S 15/8997* (2013.01); *G10K 11/346* (2013.01)

(58) Field of Classification Search
CPC ................................ A61B 8/13; A61B 8/4494
See application file for complete search history.

(56) References Cited

U.S. PATENT DOCUMENTS

| | | |
|---|---|---|
| 4,596,145 A | 6/1986 | Smith et al. |
| 4,694,434 A | 9/1987 | von Ramm et al. |

(Continued)

FOREIGN PATENT DOCUMENTS

| | | |
|---|---|---|
| CN | 1575771 A | 2/2005 |
| CN | 1642485 A | 7/2005 |

(Continued)

OTHER PUBLICATIONS

Communication dated May 19, 2015, issued by the European Patent Office in counterpart European Patent Application No. 14197627.4.

(Continued)

*Primary Examiner* — Joseph M Santos Rodriguez
(74) *Attorney, Agent, or Firm* — Sughrue Mion, PLLC

(57) ABSTRACT

The ultrasonic diagnostic apparatus includes an ultrasonic transducer array in which ultrasonic transducer elements are two-dimensionally arranged; and a controller configured to control the ultrasonic transducer elements to transmit ultrasonic signals and control the ultrasonic transducer elements arranged in rows of the ultrasonic transducer array to sequentially receive ultrasonic echo signals.

21 Claims, 14 Drawing Sheets

(51) Int. Cl.
*A61B 8/14* (2006.01)
*A61B 8/08* (2006.01)

(56) References Cited

U.S. PATENT DOCUMENTS

| | | | |
|---|---|---|---|
| 5,161,537 A * | 11/1992 | Hashimoto | A61B 8/00 600/447 |
| 5,229,933 A | 7/1993 | Larson, III | |
| 5,546,807 A | 8/1996 | Oxaal et al. | |
| 5,722,412 A | 3/1998 | Pflugrath et al. | |
| 6,241,675 B1 | 6/2001 | Smith et al. | |
| 6,416,475 B1 | 7/2002 | Hwang et al. | |
| 6,500,123 B1 | 12/2002 | Holloway et al. | |
| 2002/0045830 A1 | 4/2002 | Powers et al. | |
| 2003/0163046 A1 | 8/2003 | Nohara et al. | |
| 2003/0220554 A1 | 11/2003 | Grenon et al. | |
| 2004/0064048 A1 | 4/2004 | Li | |
| 2004/0138564 A1 | 7/2004 | Hwang et al. | |
| 2005/0124880 A1 * | 6/2005 | Shinomura | A61B 8/13 600/437 |
| 2005/0243812 A1 | 11/2005 | Phelps | |
| 2007/0161904 A1 * | 7/2007 | Urbano | A61B 8/00 600/459 |
| 2008/0027320 A1 * | 1/2008 | Bolorforosh | A61B 8/12 600/439 |
| 2011/0172537 A1 | 7/2011 | Hongou et al. | |
| 2012/0302883 A1 * | 11/2012 | Kong | A61N 7/02 600/439 |

FOREIGN PATENT DOCUMENTS

| | | |
|---|---|---|
| CN | 1856273 A | 11/2006 |
| CN | 1856274 A | 11/2006 |
| CN | 1894598 A | 1/2007 |
| CN | 102138807 A | 8/2011 |
| JP | 2009090129 A | 4/2009 |
| JP | 2011050491 A | 3/2011 |

OTHER PUBLICATIONS

Park, Suhyun, et. al, "Beamforming and Imageforming for 3D Ultrasound Imaging System using 2-D CMUT-on-ASIC Arrays", 2013 IEEE International Ultrasonics Symposium, Jul. 21, 2013, p. 1448-1451, XP055187790.

Kim, Bae-Hyung, et. al, "Volumetric ultrasound image-forming using fully controllable 2-D CMUT-on-ASIC arrays", Proceedings of SPIE Digital Library, Mar. 29, 2013, vol. 8675, p. 86750A1-86750A8, XP055187736.

Communication dated Oct. 11, 2017, issued by the European Patent Office in counterpart European Patent Application No. 14197627.4.

Communication dated Jul. 27, 2018, issued by the State Intellectual Property Office of P.R. China in counterpart Chinese Application No. 201410759495.6.

Park, S., et al., "Beamforming and Imageforming for 3D Ultrasound Imaging System using 2-D CMUT-on-ASIC Arrays", Dec. 31, 2013, Joint UFFC, EFTF and PFM Symposium, p. 1448-1451, 4 pages total.

Communication dated Apr. 3, 2019 issued by the State Intellectual Property Office of P.R. China in counterpart Chinese Application No. 201410759495.6.

Communication dated Mar. 14, 2019 issued by the European Intellectual Property Office in counterpart European Application No. 14 197 627.4.

* cited by examiner

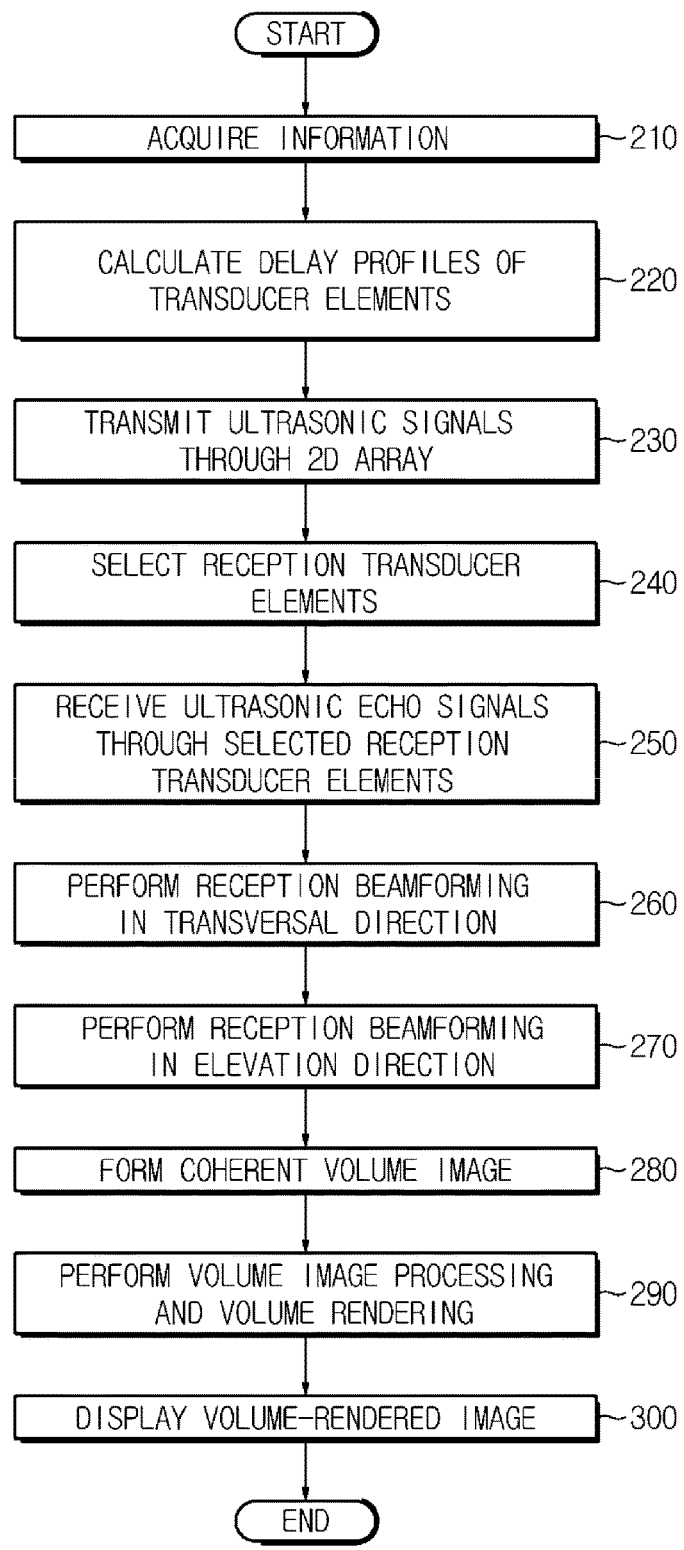

ULTRASONIC DIAGNOSTIC APPARATUS AND CONTROL METHOD THEREOF

CROSS-REFERENCE TO RELATED APPLICATION

This application claims priority from Korean Patent Application No. 10-2013-0154977, filed on Dec. 12, 2013 in the Korean Intellectual Property Office, the disclosure of which is incorporated herein by reference in its entirety.

BACKGROUND

1. Field

Exemplary embodiments relate to generating an ultrasound image of an object.

2. Description of the Related Art

In general, an ultrasonic diagnostic apparatus applies an ultrasonic signal from the surface of an object, for example, a human body, to a target site inside the object, and non-invasively acquires tomograms of soft tissues or images regarding blood flow using information of reflected ultrasonic signals, i.e., ultrasonic echo signals. The ultrasonic diagnostic apparatus displays images in real time and may be used for heart, abdomen, urinary, and obstetric and gynecologic diagnosis.

Related art ultrasonic diagnostic apparatuses mostly provide information of cross-sections of an object through two-dimensional (2D) images using a one dimensional (1D) transducer array and acquire three-dimensional (3D) volume information of the object while shifting the 1D transducer array with hands of a user, i.e., free-hand scan, or mechanically, i.e., mechanical scan.

However, performance of such a 3D image acquisition method through free-hand scan or mechanical scan of the 1D transducer array is restrictive in terms of an image generation speed, i.e., temporal resolution or spatial resolution, and, thus, interest in 3D image acquisition techniques using a 2D transducer array has increased.

In order to use 3D imaging, which may be achieved using the 2D transducer array, improvement in resolution and scanning speed of the images (improvement in system performance) and a compact system size (prevention of increase in system complexity) should be achieved. However, existing systems are limited in satisfaction of all of these requirements.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an ultrasonic diagnostic apparatus which, when 3D ultrasonic images are generated using a 2D ultrasonic transducer array, may improve resolution and scanning speed of the images, and a control method thereof.

One or more exemplary embodiments provide an ultrasonic diagnostic apparatus which, when 3D ultrasonic images are generated using a 2D ultrasonic transducer array, may generate 3D ultrasonic images of an object even with a compact system having a relatively low complexity and a control method thereof.

In accordance with an aspect of an exemplary embodiment, an ultrasonic diagnostic apparatus includes a 2D ultrasonic transducer array in which a plurality of ultrasonic transducer elements is two-dimensionally arranged, and a controller controlling all of the ultrasonic transducer elements of the 2D ultrasonic transducer array to transmit ultrasonic signals and controlling the ultrasonic transducer elements of one of rows of the 2D ultrasonic transducer array to sequentially receive ultrasonic echo signals.

The controller may control all of the ultrasonic transducer elements of the 2D ultrasonic transducer array to transmit defocused plane waves, in transmission of the ultrasonic signals.

The controller may control the ultrasonic transducer elements of one of rows of the 2D ultrasonic transducer array to sequentially transmit defocused plane waves, in transmission of the ultrasonic signals.

The controller may control all of the ultrasonic transducer elements of the 2D ultrasonic transducer array transmit ultrasonic waves and perform fixed focusing of the ultrasonic waves, in transmission of the ultrasonic signals.

The controller may control the ultrasonic transducer elements of one of rows of the 2D ultrasonic transducer array to sequentially transmit ultrasonic waves and perform fixed focusing of the ultrasonic waves, in transmission of the ultrasonic signals.

The controller may control one or plural ultrasonic transducer elements of one of rows of the 2D ultrasonic transducer array to sequentially receive the ultrasonic echo signals, in reception of the ultrasonic echo signals.

The controller may control rows of the 2D ultrasonic transducer array to be sequentially switched one by one so as to receive the ultrasonic echo signals while shifting the position of the switched row in the elevation direction, in reception of the ultrasonic echo signals.

The controller may prepare a plurality of ultrasonic transducer elements arranged in the elevation direction and forming one column, and control the ultrasonic transducer elements of one of rows of the 2D ultrasonic transducer array to generate ultrasonic echo signals for reception beamforming in the elevation direction by sequentially using the ultrasonic echo signals.

The controller may control execution of dynamic reception focusing or synthetic aperture focusing in the elevation direction using the generated ultrasonic echo signals for reception beamforming in the elevation direction.

The controller may control execution of volume beamforming by sequentially using the ultrasonic transducer elements of one of rows of the 2D ultrasonic transducer array based on the ultrasonic echo signals or the generated ultrasonic echo signals for reception beamforming in the elevation direction.

In accordance with an aspect of an exemplary embodiment, a control method of an ultrasonic diagnostic apparatus having a 2D ultrasonic transducer array in which a plurality of ultrasonic transducer elements is two-dimensionally arranged includes controlling all of the ultrasonic transducer elements of the 2D ultrasonic transducer array to transmit ultrasonic signals and controlling the ultrasonic transducer elements of one of rows of the 2D ultrasonic transducer array to sequentially receive ultrasonic echo signals.

In the control of all of the ultrasonic transducer elements of the 2D ultrasonic transducer array to transmit ultrasonic signals, all of the ultrasonic transducer elements of the 2D ultrasonic transducer array may be controlled to transmit defocused plane waves.

In the control of all of the ultrasonic transducer elements of the 2D ultrasonic transducer array to transmit ultrasonic signals, the ultrasonic transducer elements of one of rows of the 2D ultrasonic transducer array may be controlled to sequentially transmit defocused plane waves.

In the control of all of the ultrasonic transducer elements of the 2D ultrasonic transducer array to transmit ultrasonic signals, all of the ultrasonic transducer elements of the 2D ultrasonic transducer array may be controlled to transmit ultrasonic waves and perform fixed focusing of the ultrasonic waves.

In the control of all of the ultrasonic transducer elements of the 2D ultrasonic transducer array to transmit ultrasonic signals, the ultrasonic transducer elements of one of rows of the 2D ultrasonic transducer array may be controlled to sequentially transmit ultrasonic waves and perform fixed focusing of the ultrasonic waves.

In the control of the ultrasonic transducer elements of one of rows of the 2D ultrasonic transducer array to sequentially receive ultrasonic echo signals, one or plural ultrasonic transducer elements of one of rows of the 2D ultrasonic transducer array may be controlled to sequentially receive the ultrasonic echo signals.

In the control of the ultrasonic transducer elements of one of rows of the 2D ultrasonic transducer array to sequentially receive ultrasonic echo signals, rows of the 2D ultrasonic transducer array may be sequentially switched one by one so as to receive the ultrasonic echo signals while shifting the position of the switched row in the elevation direction.

The control method may further include preparing a plurality of ultrasonic transducer elements arranged in the elevation direction and forming one column and controlling the ultrasonic transducer elements of one of rows of the 2D ultrasonic transducer array to generate ultrasonic echo signals for reception beamforming in the elevation direction by sequentially using the ultrasonic echo signals.

Dynamic reception focusing or synthetic aperture focusing in the elevation direction may be executed using the generated ultrasonic echo signals for reception beamforming in the elevation direction.

Volume beamforming may be executed by sequentially using the ultrasonic transducer elements of one of rows of the 2D ultrasonic transducer array based on the ultrasonic echo signals or the generated ultrasonic echo signals for reception beamforming in the elevation direction.

BRIEF DESCRIPTION OF THE DRAWINGS

The above and/or other aspects will become more apparent by describing certain exemplary embodiments with reference to the accompanying drawings, in which:

FIG. 11 is a flowchart illustrating a control method of the ultrasonic diagnostic apparatus.

DETAILED DESCRIPTION

Figure 1:
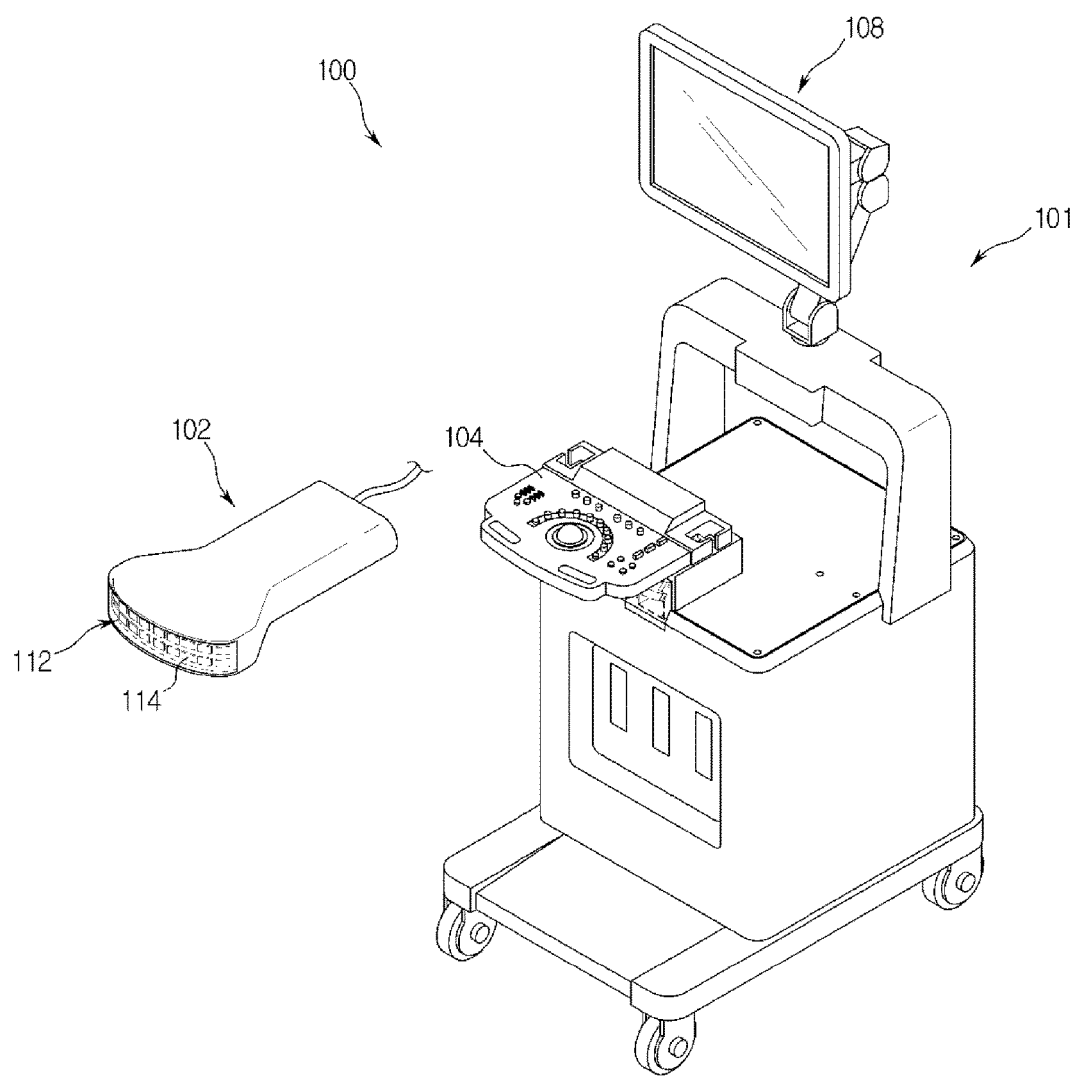
FIG. 1 is a view illustrating an ultrasonic diagnostic apparatus.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

FIG. 1 is a view illustrating an ultrasonic diagnostic apparatus.

As exemplarily shown in FIG. 1, an ultrasonic diagnostic apparatus 100 may include an ultrasonic probe 102 transmitting ultrasonic waves to an object, receiving echo ultrasonic waves from the object, and converting the echo ultrasonic waves into electrical signals, i.e., ultrasonic signals, and a main body 101 connected to the ultrasonic probe 102 and provided with an input unit 104 and a display 108. An ultrasonic transducer array 112 is provided at the end portion of the ultrasonic probe 102 and includes a plurality of ultrasonic transducer elements 114. The plurality of ultrasonic transducer elements 114 may be arranged in a linear array or be arranged in a convex array.

Figure 2:
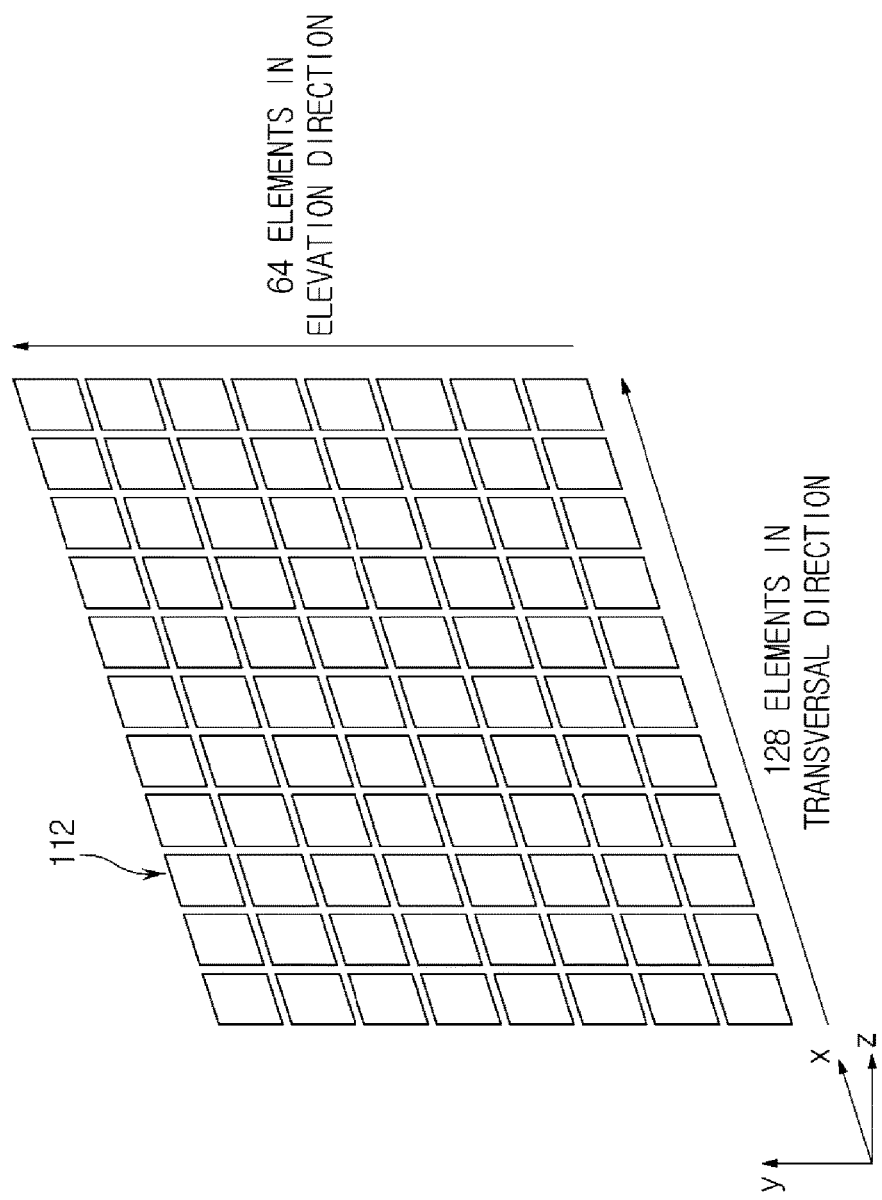
FIG. 2 is a view illustrating the structure and arrangement direction of a 2D ultrasonic transducer array.

FIG. 2 is a view illustrating the structure and arrangement direction of a 2D ultrasonic transducer array.

As exemplarily shown in FIG. 2, the 2D ultrasonic transducer array 112 has a structure in which total of L ultrasonic transducer elements 114 are two-dimensionally arranged as M×N array. In an exemplary embodiment, a 2D ultrasonic transducer array 112 including total of 8,192 (64×128) ultrasonic transducer elements 114 is illustrated. For example, a transversal direction, i.e., azimuth direction, is defined as an X-axis, an elevation direction is defined as a Y-axis, and an axial direction, i.e., depth direction, is defined as a Z-axis-. A number N of ultrasonic transducer elements 114 arranged in one row in the transversal direction, i.e., X-axis direction is 128, and a number M of ultrasonic transducer elements 114 arranged in one column in the elevation direction, i.e., Y-axis direction, is 64. Further, the ultrasonic signals transmitted from the respective ultrasonic transducer elements 114 of the 2D ultrasonic transducer array 112 proceed in the axial direction, i.e., Z-axis direction.

Various 3D ultrasonic scanning methods and transmission/reception beamforming methods using the 2D ultrasonic transducer array 112 using the M×N ultrasonic transducer elements 114 shown in FIG. 2 are described in detail below.

Figure 3:
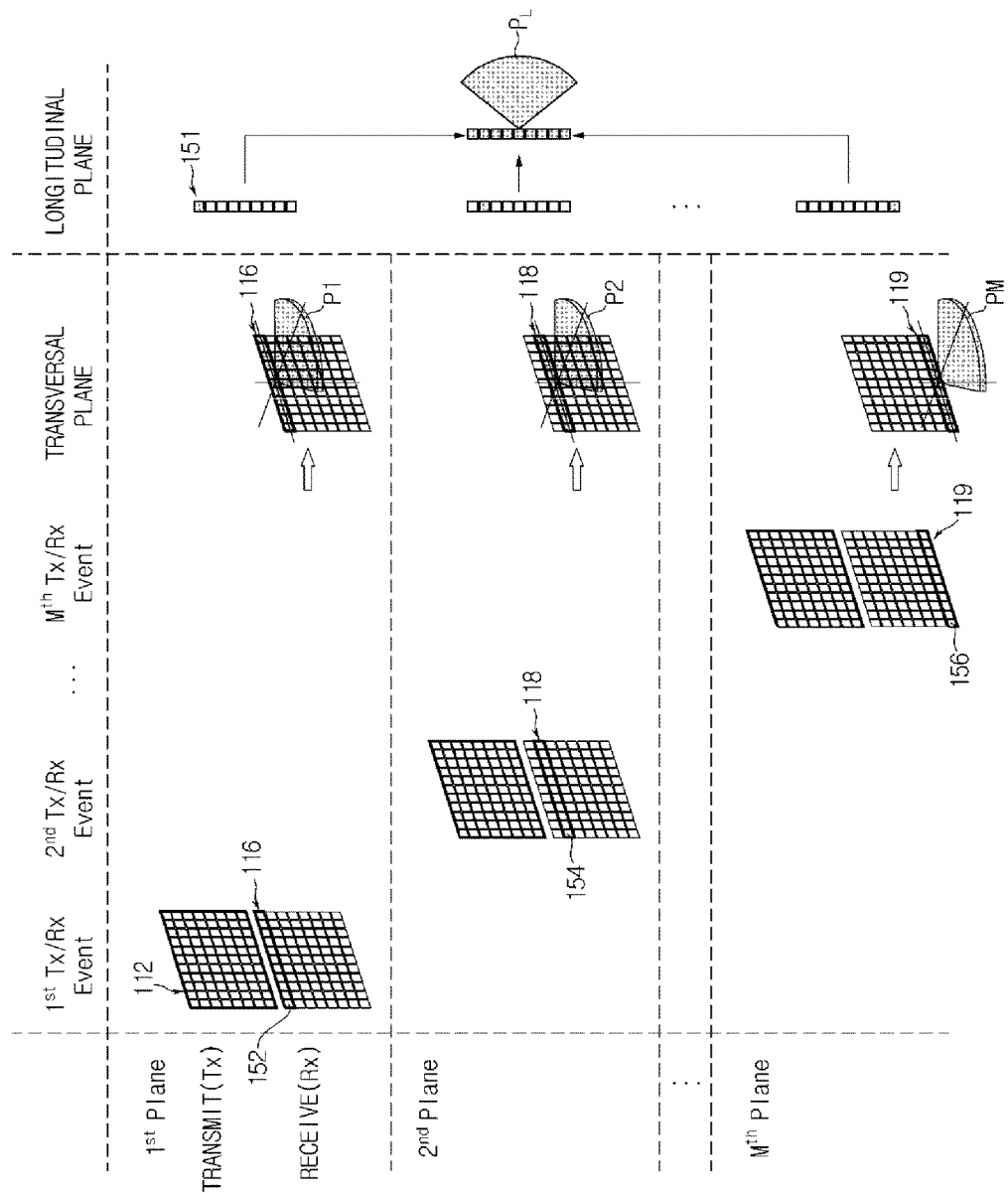
FIGS. 3, 4, 5, 6, 7, and 8 are views exemplarily illustrating various 3D ultrasonic scanning methods and transmission/reception beamforming methods using the 2D ultrasonic transducer array.

FIG. 3 is a view illustrating a method in which defocused plane waves are transmitted using the 2D ultrasonic transducer array, reflected signals are received using ultrasonic transducer elements 114 of the respective rows of the 2D ultrasonic transducer array, and dynamic reception focusing is performed using the received signals. In FIG. 3, portions shown by a thick solid line indicate active elements or active channels. Further, in FIG. 3, among 2D ultrasonic transducer arrays illustrated in parallel in the vertical direction, the upper 2D ultrasonic transducer array represents the array during transmission (Tx) and the lower 2D ultrasonic transducer array represents the same array during reception (Rx).

Referring to FIG. 3, in a first Tx/Rx event, defocused plane waves are transmitted through all of the ultrasonic transducer elements 114 of the 2D ultrasonic transducer array 112, ultrasonic echo signals are received through the ultrasonic transducer elements 114 of the first row 116 of the 2D ultrasonic transducer array 112, and thus, a first plane P1, i.e., a transversal plane P1, formed by the signals received through the ultrasonic transducer elements 114 of the first row 116 of the 2D ultrasonic transducer array 112, may be acquired.

Next, in a second Tx/Rx event, defocused plane waves are transmitted through all of the ultrasonic transducer elements 114 of the 2D ultrasonic transducer array 112, ultrasonic echo signals are received through the ultrasonic transducer elements 114 of the second row 118 of the 2D ultrasonic transducer array 112, and thus, a second plane P2, i.e., a transversal plane P2, formed by the signals received through the ultrasonic transducer elements 114 of the second row 118 of the 2D ultrasonic transducer array 112, may be acquired.

Consequently, in an $M^{th}$ Tx/Rx event, for example, a $64^{th}$ event, defocused plane waves are transmitted through all of the ultrasonic transducer elements 114 of the 2D ultrasonic transducer array 112, ultrasonic echo signals are received through the ultrasonic transducer elements 114 of the $M^{th}$ row 119 of the 2D ultrasonic transducer array 112, and thus, an $M^{th}$ plane PM, i.e., a transversal plane PM, formed by the signals received through the ultrasonic transducer elements 114 of the $M^{th}$ row 119 of the 2D ultrasonic transducer array 112, may be acquired.

When ultrasonic echo signals are received, N ultrasonic transducer elements of each of the rows 116, 118, . . . , 119 of the 2D ultrasonic transducer array 112 are sequentially switched, for example, 128 ultrasonic transducer elements arranged in the transversal direction are switched. For example, the switching of the transducer elements is performed in the first row, in the second row, . . . , in the $M^{th}$ row, and thus, the ultrasonic echo signals are received while also shifting the position of the receiving transducer elements in the elevation direction.

Referring to the right side of FIG. 3, M ultrasonic transducer elements 114 in the elevation direction of one column are illustrated. The ultrasonic data for reception beam focusing in the elevation direction are formed by using the ultrasonic echo signals sequentially received in an order of the respective rows of the 2D ultrasonic transducer array 112.

That is, the ultrasonic echo signals sequentially received from the respective rows 116, 118, . . . , 119 of the 2D ultrasonic transducer array 112 are arranged in the elevation direction and sequentially stored in positions corresponding to ultrasonic transducer elements of one column to form a full aperture in the elevation direction, and dynamic reception focusing or synthetic aperture focusing in the elevation direction is performed using the full aperture, thus generating a longitudinal plane $P_L$.

That is, one column 151, i.e., a virtual column, in the elevation direction is formed by storing an ultrasonic echo signal, received through the first ultrasonic transducer 152 of the first row 116, at a position corresponding to the first ultrasonic transducer 152 of the column 151, storing an ultrasonic echo signal, received through the second ultrasonic transducer 156 of the second row 118, at a position corresponding to the second ultrasonic transducer 156 of the column 151, . . . , and storing an ultrasonic echo signal, received through the Mth ultrasonic transducer 156 of the $M^{th}$ row 119, at a position corresponding to the $M^{th}$ ultrasonic transducer 158 the column 151. In this manner, all of the columns of the elevation direction in correspondence to the ultrasonic transducer 112 are acquired and the dynamic reception focusing or synthetic aperture focusing in the elevation direction is performed using the full aperture, thus generating a longitudinal plane $P_L$.

When M transmission/reception events, for example, 64 events, are completed, 3D beamforming and 3D image generation of a region of interest (ROI) may be performed using the transversal planes P1, P2, . . . , PM generated based on the ultrasonic echo signals received through the ultrasonic transducer elements of the respective rows 116, 118, . . . , 119 and the longitudinal plane $P_L$ generated by dynamic reception focusing or synthetic aperture focusing in the elevation direction based on the ultrasonic data in the elevation direction, formed by using the ultrasonic echo signals sequentially received according to the respective rows.

Figure 4:
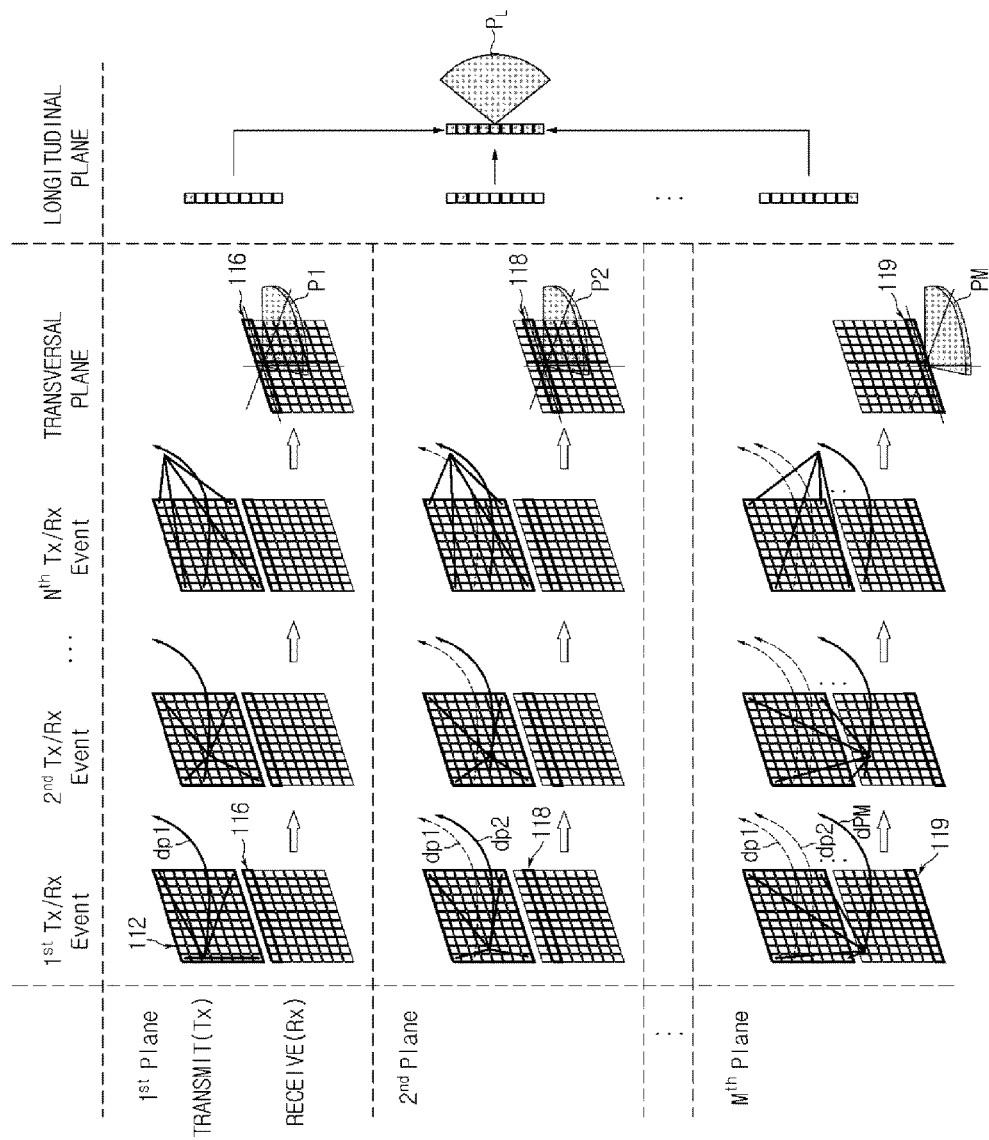

FIG. 4 is a view illustrating a method in which ultrasonic waves are transmitted, fixed, and focused using the 2D ultrasonic transducer array, reflected signals are received using ultrasonic transducer elements 114 of the respective rows of the 2D ultrasonic transducer array, and dynamic reception focusing is performed using the received signals. In FIG. 4, portions shown by a thick solid line indicate active elements or active channels. Also, in FIG. 4, among 2D ultrasonic transducer arrays illustrated in parallel in the vertical direction, the upper 2D ultrasonic transducer array represents the array during transmission (Tx) and the lower 2D ultrasonic transducer array represents the array during reception (Rx). The applicable features described above with reference to FIG. 3 will not be repeated.

Referring to FIG. 4, in order to acquire a first plane P1, i.e., a transversal plane P1, formed by signals received through the ultrasonic transducer elements 114 of the first row 112 of the 2D ultrasonic transducer array 112, in a first Tx/Rx event, ultrasonic waves are transmitted, fixed, and focused through all of the ultrasonic transducer elements 114 of the 2D ultrasonic transducer array 112 based on a first delay profile dp1 performing first angle steering, and ultrasonic echo signals are received through the ultrasonic transducer elements 114 of the first row 116 of the 2D ultrasonic transducer array 112. In a second Tx/Rx event, ultrasonic waves are transmitted, fixed, and focused through all of the ultrasonic transducer elements 114 of the 2D ultrasonic transducer array 112 based on the first delay profile dp1 performing second angle steering, and ultrasonic echo signals are received through the ultrasonic transducer elements 114 of the first row 112 of the 2D ultrasonic transducer array 112. Consequently, in an $N^{th}$ Tx/Rx event, for example, in a $128^{th}$ event if the 2D ultrasonic transducer array 112 has 128 columns, ultrasonic waves are transmitted, fixed, and focused through all of the ultrasonic transducer elements 114 of the 2D ultrasonic transducer array 112 based on the first delay profile dp1 performing $N^{th}$ angle steering, and ultrasonic echo signals are received through the ultrasonic transducer elements 114 of the first row 116 of the 2D ultrasonic transducer array 112.

Through such a method, the first plane P1, i.e., the transversal plane P1, formed by signals received through the ultrasonic transducer elements 114 of the first row 116 of the 2D ultrasonic transducer array 112, may be acquired by receiving ultrasonic echo signals through the ultrasonic transducer elements 114 of the first row 116 of the 2D ultrasonic transducer array 112 and performing dynamic reception focusing of the received ultrasonic echo signals.

Next, in order to acquire a second plane P2, i.e., a transversal plane P2, formed by signals received through the ultrasonic transducer elements 114 of the second row 118 of the 2D ultrasonic transducer array 112, in a first Tx/Rx event, ultrasonic waves are transmitted, fixed, and focused through all of the ultrasonic transducer elements 114 of the 2D ultrasonic transducer array 112 based on a second delay profile dp2 performing first angle steering, and ultrasonic echo signals are received through the ultrasonic transducer elements 114 of the second row 118 of the 2D ultrasonic transducer array 112. In a second Tx/Rx event, ultrasonic waves are transmitted, fixed, and focused through all of the ultrasonic transducer elements 114 of the 2D ultrasonic transducer array 112 based on the second delay profile dp2 performing second angle steering, and ultrasonic echo signals are received through the ultrasonic transducer elements 114 of the second row 118 of the 2D ultrasonic transducer array 112. In an $N^{th}$ Tx/Rx event, ultrasonic waves are transmitted, fixed, and focused through all of the ultrasonic transducer elements 114 of the 2D ultrasonic transducer array 112 based on the second delay profile dp2 performing $N^{th}$ angle steering, and ultrasonic echo signals are received through the ultrasonic transducer elements 114 of the second row 118 of the 2D ultrasonic transducer array 112.

Through such a method, the second plane P2, i.e., the transversal plane P2, formed by signals received through the ultrasonic transducer elements 114 of the second row 118 of the 2D ultrasonic transducer array 112, may be acquired by receiving ultrasonic echo signals through the ultrasonic transducer elements 114 of the second row 118 of the 2D ultrasonic transducer array 112 and performing dynamic reception focusing of the received ultrasonic echo signals.

In such a manner, in order to acquire an $M^{th}$ plane PM, i.e., a transversal plane PM formed by signals received through the ultrasonic transducer elements 114 of the $M^{th}$ row 119 of the 2D ultrasonic transducer array 112, in a first Tx/Rx event, ultrasonic waves are transmitted, fixed, and focused through all of the ultrasonic transducer elements 114 of the 2D ultrasonic transducer array 112 based on an $M^{th}$ delay profile dpM performing first angle steering, and ultrasonic echo signals are received through the ultrasonic transducer elements 114 of the $M^{th}$ row 119 of the 2D ultrasonic transducer array 112.

Next, in a second Tx/Rx event, ultrasonic waves are transmitted, fixed, and focused through all of the ultrasonic transducer elements 114 of the 2D ultrasonic transducer array 112 based on the $M^{th}$ delay profile dpM performing second angle steering, and ultrasonic echo signals are received through the ultrasonic transducer elements 114 of the $M^{th}$ row 119 of the 2D ultrasonic transducer array 112. In an $N^{th}$ Tx/Rx event, ultrasonic waves are transmitted, fixed, and focused through all of the ultrasonic transducer elements 114 of the 2D ultrasonic transducer array 112 based on the $M^{th}$ delay profile dpM performing $N^{th}$ angle steering, and ultrasonic echo signals are received through the ultrasonic transducer elements 114 arranged in the $M^{th}$ row 119 forming the 2D ultrasonic transducer array 112.

Through such a method, the $M^{th}$ plane PM, i.e., the transversal plane PM formed by signals received through the ultrasonic transducer elements 114 arranged in the $M^{th}$ row 119 forming the 2D ultrasonic transducer array 112, may be acquired by receiving ultrasonic echo signals through the ultrasonic transducer elements 114 arranged in the $M^{th}$ row 119 forming the 2D ultrasonic transducer array 112 and performing dynamic reception focusing of the received ultrasonic echo signals.

As exemplarily shown on the right side of FIG. 4, M ultrasonic transducers elements arranged in the elevation direction and forming one column are provided, and ultrasonic echo signals for reception beam focusing in the height direction are formed by using the ultrasonic echo signals sequentially received in order of the respective rows forming the 2D ultrasonic transducer array 112.

Figure 5:
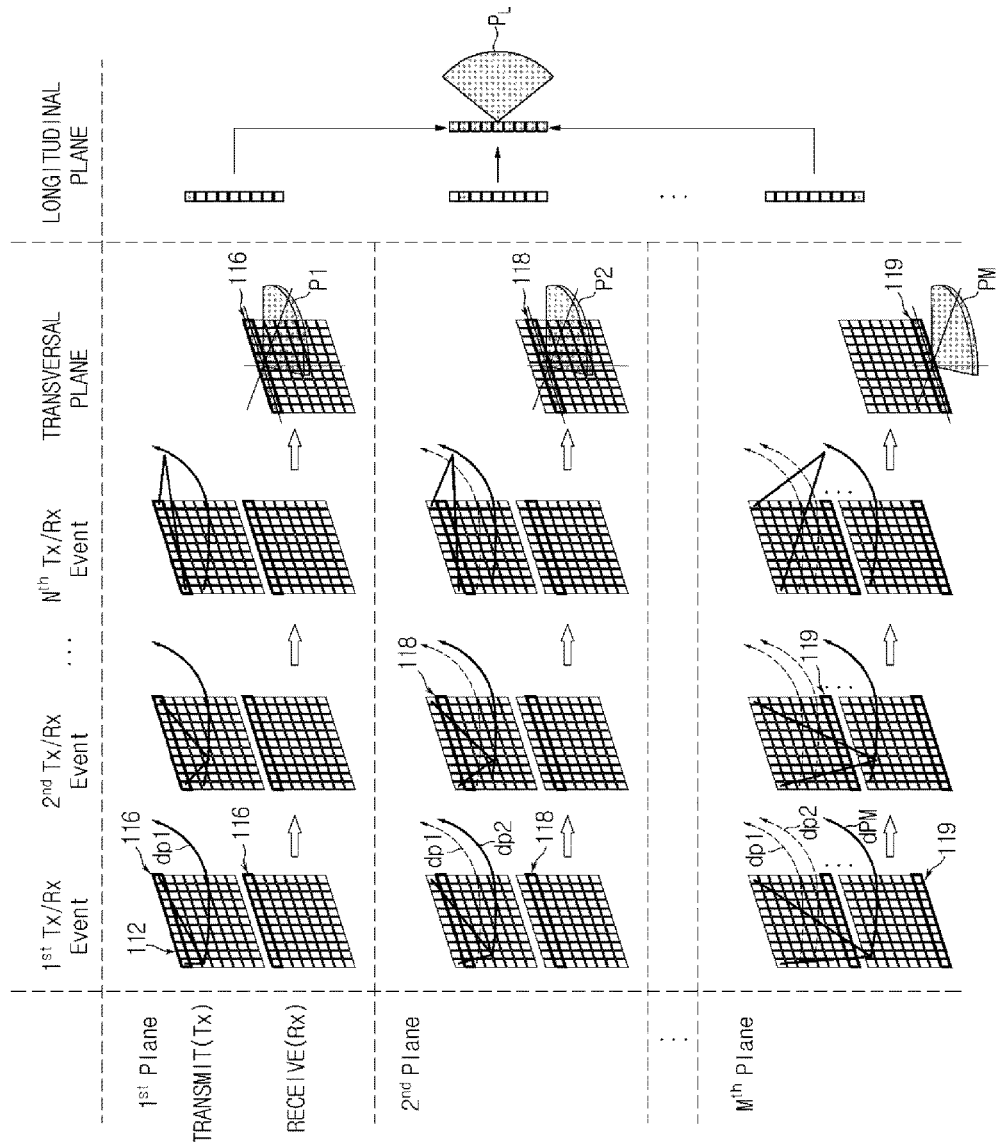

FIG. 5 is a view illustrating a method in which ultrasonic waves are transmitted, fixed, and focused by sequentially using the ultrasonic transducer elements 114 of one of the rows of the 2D ultrasonic transducer array, reflected signals are received using ultrasonic transducer elements 114 of the respective rows of the 2D ultrasonic transducer array, and dynamic reception focusing is performed using the received signals. Descriptions redundant to FIGS. 3 and 4 will be omitted.

As compared to the ultrasonic scanning method and transmission/reception beamforming method shown in FIG. 4, the ultrasonic scanning method and transmission/reception beamforming method shown in FIG. 5 is the same except that the ultrasonic waves are transmitted, fixed, and focused by sequentially using the ultrasonic transducer elements 114 of one of the rows of the 2D ultrasonic transducer array 112, i.e., the ultrasonic waves are transmitted, fixed, and focused through the ultrasonic transducer elements 114 of the first row 116, the ultrasonic waves are transmitted, fixed, and focused through the ultrasonic transducer elements 114 of the second row 118, . . . , and finally the ultrasonic waves are transmitted, fixed, and focused through the ultrasonic transducer elements 114 of the $M^{th}$ row 119.

Figure 6:
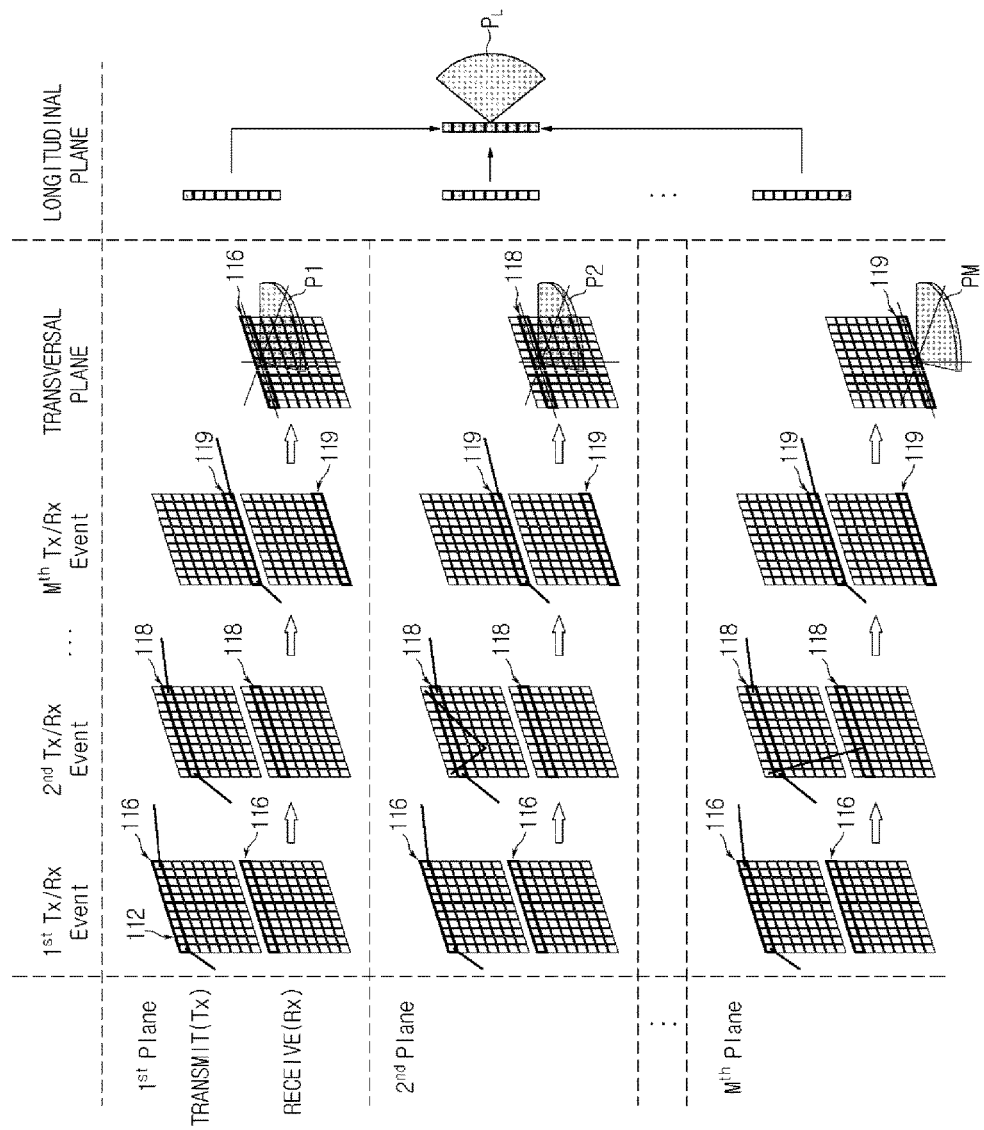

FIG. 6 is a view illustrating a method in which defocused plane waves are transmitted by sequentially using the ultrasonic transducer elements 114 of one of the rows of the 2D ultrasonic transducer array, reflected signals are received by sequentially using the ultrasonic transducer elements 114 of one of the rows of the 2D ultrasonic transducer array, and dynamic reception focusing is performed using the received signals. Descriptions redundant to FIGS. 3 to 5 will be omitted.

As exemplarily shown in FIG. 6, in order to acquire a first plane P1, i.e., a transversal plane P1, formed by signals received through the ultrasonic transducer elements 114 of the first row 116 of the 2D ultrasonic transducer array 112, in a first Tx/Rx event, defocused plane waves are transmitted through the ultrasonic transducer elements 114 of the first row 116 of the 2D ultrasonic transducer array 112, and ultrasonic echo signals are received through the ultrasonic transducer elements 114 of the first row 116 of the 2D ultrasonic transducer array 112. In a second Tx/Rx event, defocused plane waves are transmitted through the ultrasonic transducer elements 114 of the second row 118 of the 2D ultrasonic transducer array 112, and ultrasonic echo signals are received through the ultrasonic transducer elements 114 of the second row 118 of the 2D ultrasonic transducer array 112. Consequently, in an $M^{th}$ Tx/Rx event, defocused plane waves are transmitted through the ultrasonic transducer elements 114 of the $M^{th}$ row 119 of the 2D ultrasonic transducer array 112, and ultrasonic echo signals are received through the ultrasonic transducer elements 114 of the $M^{th}$ row 119 of the 2D ultrasonic transducer array 112.

Through such a method, the first plane P1, i.e., the transversal plane P1, formed by signals received through the ultrasonic transducer elements 114 of the first row 116 of the 2D ultrasonic transducer array 112, may be acquired by receiving ultrasonic echo signals through the ultrasonic transducer elements 114 of the first row 116 of the 2D ultrasonic transducer array 112 and performing dynamic reception focusing of the received ultrasonic echo signals.

In order to acquire a second plane P2, i.e., a transversal plane P2, formed by signals received through the ultrasonic transducer elements 114 of the second row 116 of the 2D ultrasonic transducer array 112, in a first Tx/Rx event, defocused plane waves are transmitted through the ultrasonic transducer elements 114 of the first row 116 of the 2D ultrasonic transducer array 112, and ultrasonic echo signals are received through the ultrasonic transducer elements 114 of the first row 116 of the 2D ultrasonic transducer array 112. In a second Tx/Rx event, defocused plane waves are transmitted through the ultrasonic transducer elements 114 of the second row 118 of the 2D ultrasonic transducer array 112, and ultrasonic echo signals are received through the ultrasonic transducer elements 114 of the second row 118 of the 2D ultrasonic transducer array 112. In an $M^{th}$ Tx/Rx event, defocused plane waves are transmitted through the ultrasonic transducer elements 114 of the $M^{th}$ row 119 of the 2D ultrasonic transducer array 112, and ultrasonic echo signals are received through the ultrasonic transducer elements 114 of the $M^{th}$ row 119 of the 2D ultrasonic transducer array 112.

Through such a method, the second plane P2, i.e., the transversal plane P2, formed by signals received through the ultrasonic transducer elements 114 of the second row 118 of the 2D ultrasonic transducer array 112, may be acquired by receiving ultrasonic echo signals through the ultrasonic transducer elements 114 of the second row 118 of the 2D ultrasonic transducer array 112 and performing dynamic reception focusing of the received ultrasonic echo signals.

Consequently, in order to acquire an $M^{th}$ plane PM, i.e., a transversal plane PM, formed by signals received through the ultrasonic transducer elements 114 of the $M^{th}$ row 119 of the 2D ultrasonic transducer array 112, in a first Tx/Rx event, defocused plane waves are transmitted through the ultrasonic transducer elements 114 of the first row 116 of the 2D ultrasonic transducer array 112, and ultrasonic echo signals are received through the ultrasonic transducer elements 114 of the first row 116 of the 2D ultrasonic transducer array 112. In a second Tx/Rx event, defocused plane waves are transmitted through the ultrasonic transducer elements 114 of the second row 118 of the 2D ultrasonic transducer array 112, and ultrasonic echo signals are received through the ultrasonic transducer elements 114 of the second row 118 of the 2D ultrasonic transducer array 112. In an $M^{th}$ Tx/Rx event, defocused plane waves are transmitted through the ultrasonic transducer elements 114 of the $M^{th}$ row 119 of the 2D ultrasonic transducer array 112, and ultrasonic echo signals are received through the ultrasonic transducer elements 114 of the $M^{th}$ row 119 of the 2D ultrasonic transducer array 112.

Through such a method, the $M^{th}$ plane PM, i.e., the transversal plane PM, formed by signals received through the ultrasonic transducer elements 114 of the $M^{th}$ row 119 of the 2D ultrasonic transducer array 112, may be acquired by receiving ultrasonic echo signals through the ultrasonic transducer elements 114 of the $M^{th}$ row 119 of the 2D ultrasonic transducer array 112 and performing dynamic reception focusing of the received ultrasonic echo signals.

As exemplarily shown on the right side of FIG. 6, M ultrasonic transducer elements 114 of the elevation direction of one column are provided, and ultrasonic echo signals for reception beam focusing in the elevation direction are formed by using the ultrasonic echo signals sequentially received in an order of the respective rows of the 2D ultrasonic transducer array 112.

Figure 7:
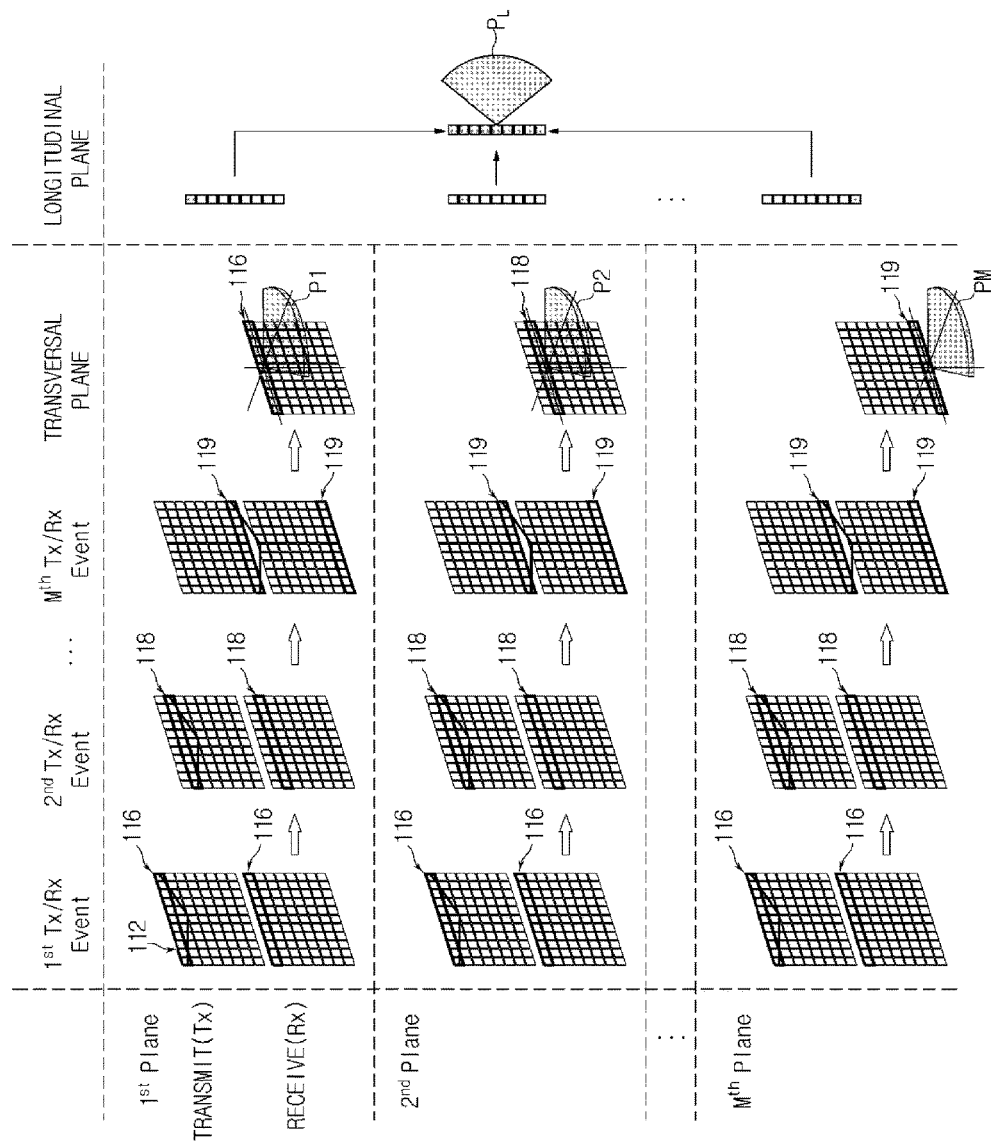

FIG. 7 is a view illustrating a method in which defocused plane waves are transmitted, fixed and focused onto a near field, i.e., a beam is dispersed and transmitted through point (single) transmission, by sequentially using the ultrasonic transducer elements 114 of one of the rows of the 2D ultrasonic transducer array, reflected signals are received by sequentially using the ultrasonic transducer elements 114 of one of the rows of the 2D ultrasonic transducer array, and dynamic reception focusing is performed using the received signals. Descriptions redundant to FIGS. 3 to 6 will be omitted.

As compared to the ultrasonic scanning method and transmission/reception beamforming method shown in FIG. 6, the ultrasonic scanning method and transmission/reception beamforming method shown in FIG. 7 is the same except that defocused plane waves are transmitted, fixed and focused onto a near field by sequentially using the ultrasonic transducer elements 114 of one of the rows of the 2D ultrasonic transducer array 112. That is, the ultrasonic waves are transmitted, fixed, and focused onto the near field through the ultrasonic transducer elements 114 of the first row 116, the ultrasonic waves are transmitted, fixed, and focused onto the near field through the ultrasonic transducer elements 114 of the second row 118, . . . , the ultrasonic waves are transmitted, fixed, and focused onto the near field through the ultrasonic transducer elements 114 of the $M^{th}$ row 119.

Figure 8:
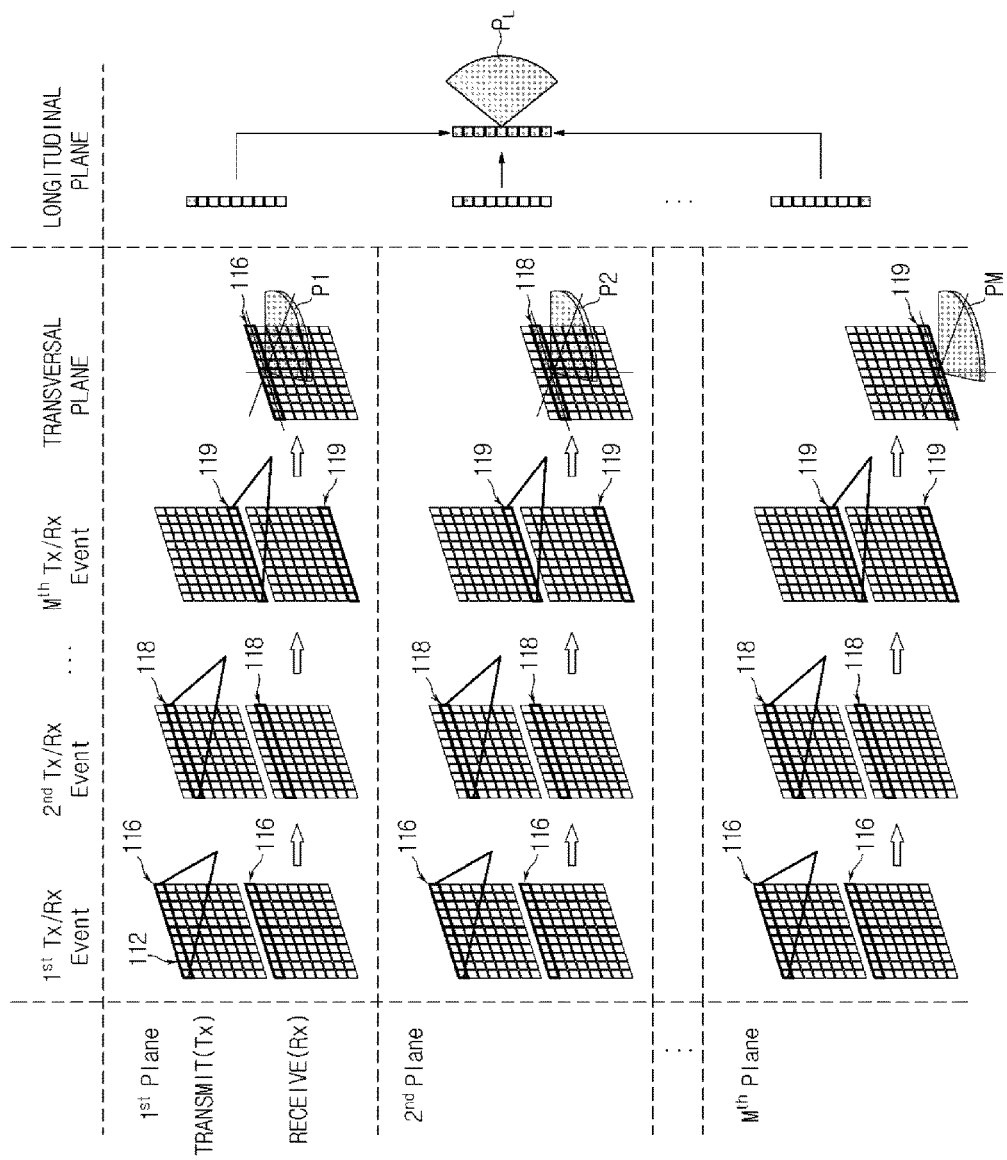

FIG. 8 is a view illustrating a method in which defocused plane waves are transmitted, fixed and focused onto a far field, i.e., a beam is dispersed and transmitted through point (single) transmission, by sequentially using the ultrasonic transducer elements 114 of one of the rows of the 2D ultrasonic transducer array, reflected signals are received by sequentially using the ultrasonic transducer elements 114 of one of the rows of the 2D ultrasonic transducer array, and dynamic reception focusing is performed using the received signals. Descriptions redundant to FIGS. 3 to 7 will be omitted.

As compared to the ultrasonic scanning method and transmission/reception beamforming method shown in FIG. 6, the ultrasonic scanning method and transmission/reception beamforming method shown in FIG. 8 is the same except that defocused plane waves are transmitted, fixed and focused onto a far field by sequentially using the ultrasonic transducer elements 114 of one of the rows of the 2D ultrasonic transducer array 112. That is, the ultrasonic waves are transmitted, fixed, and focused onto the far field through the ultrasonic transducer elements 114 of the first row 116, the ultrasonic waves are transmitted, fixed, and focused onto the far field through the ultrasonic transducer elements 114 of the second row 118, . . . , the ultrasonic waves are transmitted, fixed, and focused onto the far field through the ultrasonic transducer elements 114 of the $M^{th}$ row 119. Therefore, a detailed description of the ultrasonic scanning method and transmission/reception beamforming method shown in FIG. 8 will be omitted.

As described above with reference to FIGS. 3 to 8, ultrasonic echo signals are received by sequentially using the ultrasonic transducer elements 114 of one of the rows 116 to 119 of the 2D ultrasonic transducer array 112. However, ultrasonic echo signals do not need to be received using the ultrasonic transducer elements 114 of all of the rows of the 2D ultrasonic transducer array 112, and may be received by sequentially using only the ultrasonic transducer elements 114 of the first, third, fifth, . . . rows, i.e., only the ultrasonic transducers of the odd-numbered rows, or sequentially using only the ultrasonic transducer elements of the second, fourth, sixth, . . . rows, i.e., only the ultrasonic transducer elements of the even-numbered rows.

Further, when ultrasonic echo signals are received by sequentially using the ultrasonic transducer elements 114 of one of the rows 116 to 119 of the 2D ultrasonic transducer array 112, all of the ultrasonic transducer elements 114 of each row may be used or one or several ultrasonic transducer elements 114 of each row may be used.

Setting of rows to be used in reception of ultrasonic echo signals, for example, all of the rows forming the odd-numbered rows, or the even-numbered rows, and the number of ultrasonic transducer elements 114 in each row to be used, for example, five ultrasonic transducers or one transducer in each row, closely relates to scanning speed and beamforming performance. That is, when the number of rows to be used in reception of ultrasonic echo signals or the number of ultrasonic transducer elements 114 in each row to be used is small, scanning speed is improved but beamforming performance is lowered, and when the number of rows to be used in reception of ultrasonic echo signals or the number of ultrasonic transducer elements 114 in each row to be used is large, beamforming performance is improved but scanning speed is lowered. The display 108 displays particulars, necessary for a user to set the number of rows to be used in reception of ultrasonic echo signals and the number of ultrasonic transducer elements 114 in each row to be used to perform selection between scanning speed and beamforming performance, through a graphical user interface (GUI).

Figure 9A:
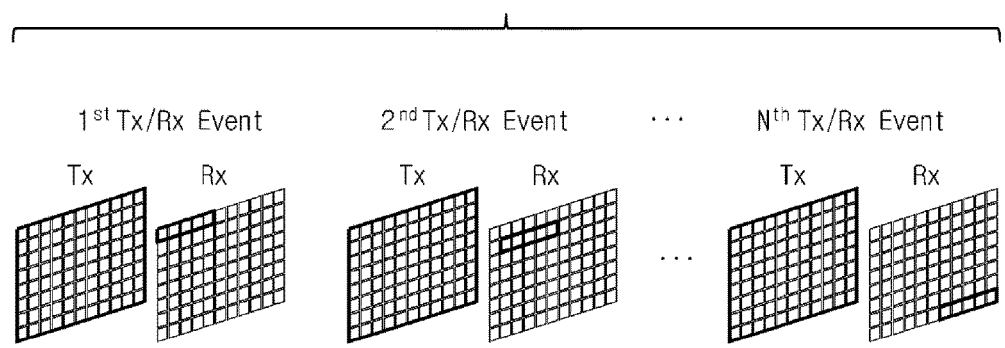
FIGS. 9A, 9B, 9C, and 9D are views exemplarily illustrating various ultrasonic transmission/reception methods for 3D ultrasonic scanning using the 2D ultrasonic transducer array.

In an example illustrated in FIG. 9A, ultrasonic waves are transmitted through all of the ultrasonic transducer elements 114 of the ultrasonic transducer array 112, and ultrasonic echo signals are received by sequentially using the ultrasonic transducer elements 114 of one of the rows of the ultrasonic transducer array 112, while the ultrasonic echo signals are received by using only five ultrasonic transducer elements 114 of one row. As the Tx/Rx events proceed, the positions of five transducer elements in each row used in reception of ultrasonic echo signals shift in the rightward direction by one column.

Figure 9B:
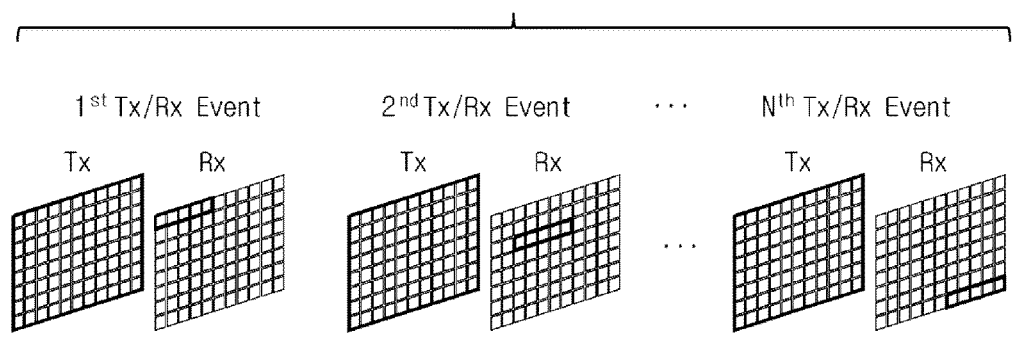

In an example illustrated in FIG. 9B, ultrasonic waves are transmitted through all of the ultrasonic transducer elements 114 of the ultrasonic transducer array 112, and ultrasonic echo signals are received by sequentially using the ultrasonic transducer elements 114 of one of the odd-numbered rows of the ultrasonic transducer array 112, while the ultrasonic echo signals are received by using only five ultrasonic transducer elements 114 of one row. As the Tx/Rx events proceed, the positions of five transducer elements in each odd-numbered row used in reception of ultrasonic echo signals shift in the rightward direction by two columns.

The ultrasonic transmission/reception method for 3D ultrasonic scanning shown in FIG. 9A has lower scanning speed but has higher beamforming performance as compared to that of FIG. 9B.

Figure 9C:
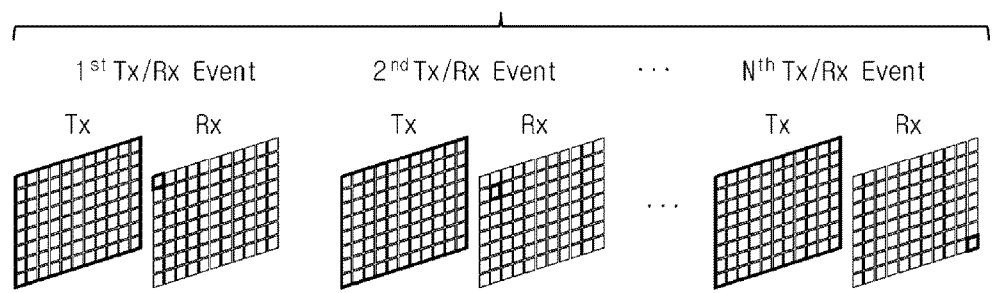

Further, in an example illustrated in FIG. 9C, ultrasonic waves are transmitted through all of the ultrasonic transducer elements 114 of the ultrasonic transducer array 112, and ultrasonic echo signals are received by sequentially using the ultrasonic transducer elements 114 of one of the rows of the ultrasonic transducer array 112, while an ultrasonic echo signal is received by using only one of the ultrasonic transducer elements 114 of one row. As the Tx/Rx events proceed, the position of one transducer in each row used in reception of ultrasonic echo signals shifts in the rightward direction by one column.

Figure 9D:
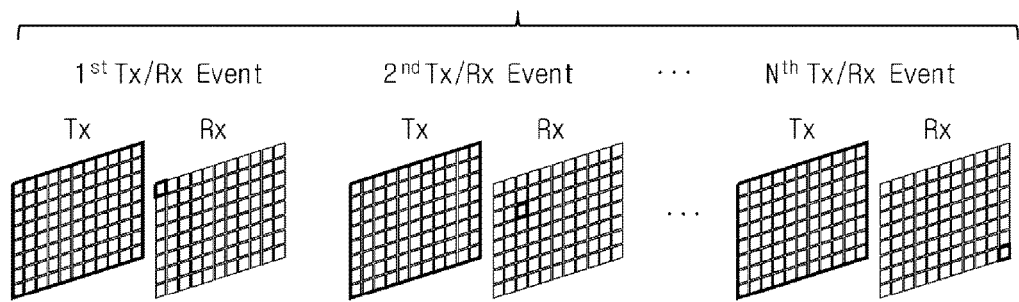

In an example illustrated in FIG. 9D, ultrasonic waves are transmitted through all of the ultrasonic transducer elements 114 of the ultrasonic transducer array 112, and ultrasonic echo signals are received by sequentially using the ultrasonic transducer elements 114 of one of the odd-numbered rows of the ultrasonic transducer array 112, while an ultrasonic echo signal is received by using only one of the ultrasonic transducer elements 114 of one row. As the Tx/Rx events proceed, the position of one transducer in each row used in reception of ultrasonic echo signals shifts in the rightward direction by two columns.

The ultrasonic transmission/reception method for 3D ultrasonic scanning shown in FIG. 9C has lower scanning speed but has higher beamforming performance as compared to that of FIG. 9D.

Figure 10:
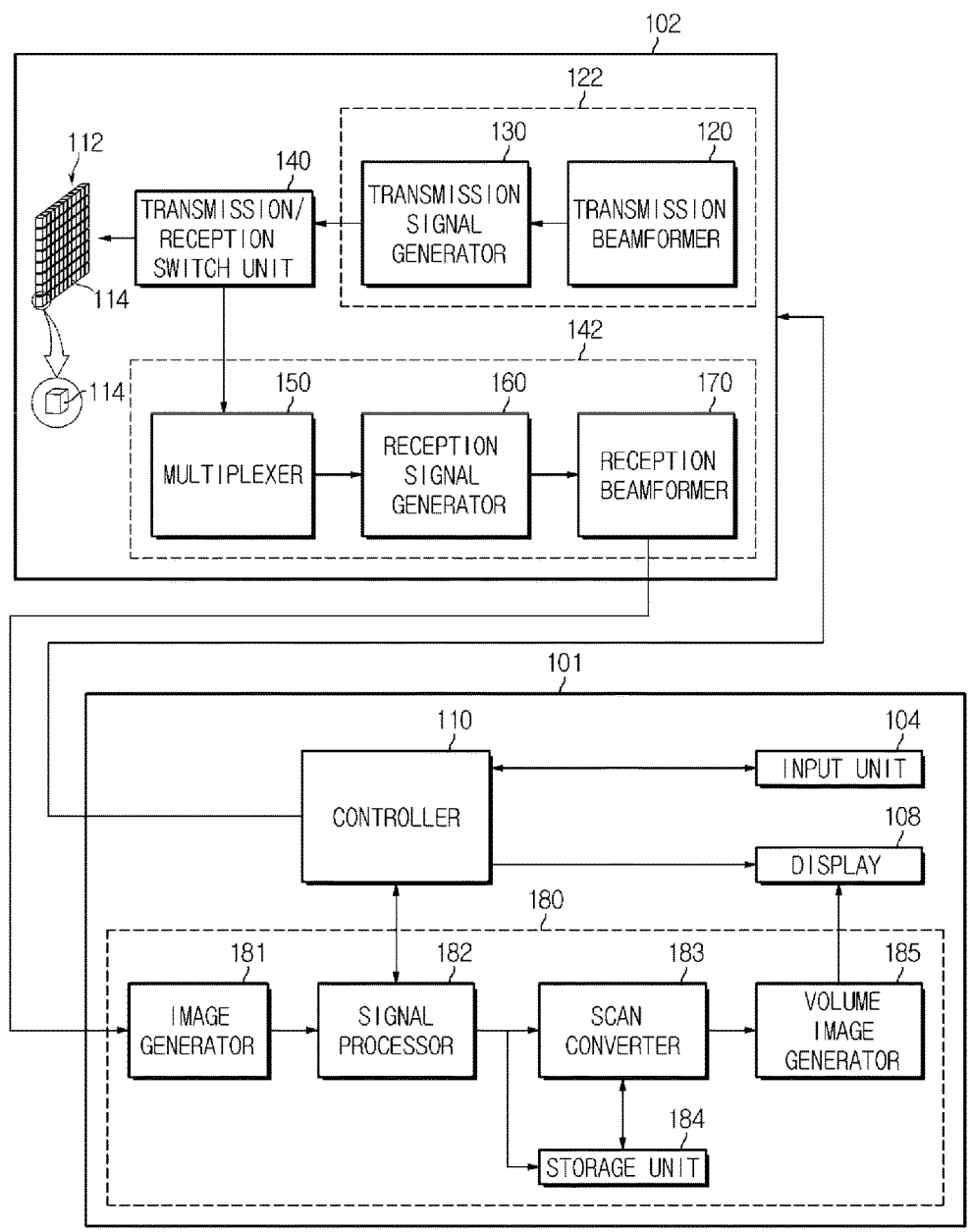
FIG. 10 is a control block diagram of the ultrasonic diagnostic apparatus.

FIG. 10 is a control block diagram of the ultrasonic diagnostic apparatus.

As exemplarily shown in FIG. 10, the ultrasonic probe 102 may include an ultrasonic transducer array 112, an ultrasonic transmitter 122, a transmission/reception switch unit 140, and an ultrasonic receiver 142. The main body 101 may include a controller 110, an image processor 180, an input unit 104, and a display 108. The features described above with reference to FIGS. 1 to 9 are applicable here and will not be repeated.

The ultrasonic transducer array 112 may include ultrasonic transducer elements 114 which generate ultrasonic waves according to applied voltage or current, transmit the generated ultrasonic waves to at least one target site in an object, receive echo ultrasonic waves reflected by the target site, and convert the received echo ultrasonic waves into electrical signals. The ultrasonic transducer array 112 may be a 2D ultrasonic transducer array 112 in which the plurality of ultrasonic transducer elements 114 is two-dimensionally arranged, for example, in a planar fashion, as exemplarily shown in FIG. 10.

An ultrasonic transducer may convert electrical energy into wave energy and/or convert wave energy into electrical energy. The ultrasonic transducer may perform functions of both an ultrasonic generation element and an ultrasonic reception element.

The ultrasonic transducer array 112 generates ultrasonic waves while vibrating due to a pulse signal applied to the ultrasonic transducer array 112 according to a control signal from a controller 110 provided in the main body 101 or by AC current. The generated ultrasonic waves are transmitted to the target site in the object. The ultrasonic waves generated from the ultrasonic transducer array 112 may be focused and transmitted to a plurality of target sites within the object. That is, the generated ultrasonic waves may be multi-focused and transmitted to the plurality of target sites.

The ultrasonic waves generated from the ultrasonic transducer array 112 are reflected by at least one target site in the object and return to the ultrasonic transducer array 112. The ultrasonic transducer array 112 receives the echo ultrasonic waves reflected by the target site. When the echo ultrasonic waves reach the ultrasonic transducer array 112, the ultrasonic transducer array 112 vibrates at a designated frequency corresponding to the frequency of the echo ultrasonic waves, and outputs AC current of a frequency corresponding to the vibrating frequency of the ultrasonic transducer array 112. Thereby, the ultrasonic transducer array 112 may convert the received echo ultrasonic waves into electrical signals.

Since each of the ultrasonic transducer elements 114 receives external ultrasonic waves and outputs an electrical signal, the ultrasonic transducer array 112 may output electrical signals of multiple channels. For example, the number of the channels is the same as the number of the ultrasonic transducer elements 114 of the ultrasonic transducer array 112.

The ultrasonic transducer elements 114 may include a piezoelectric vibrator or a thin film. If AC current from an external power supply device or an internal electrical storage device, for example, a power source (not shown), such as a battery, is applied to the piezoelectric vibrator or the thin film of one or all of the ultrasonic transducer elements 114, the piezoelectric vibrator or the thin film vibrates at a designated frequency according to the applied AC current and ultrasonic waves of a designated frequency are generated according to the vibrating frequency. On the other hand, if echo ultrasonic waves of a designated frequency reach the piezoelectric vibrator or the thin film, the piezoelectric vibrator or the thin film vibrates according to the echo ultrasonic waves. For example, the piezoelectric vibrator or the thin film outputs AC current of a frequency corresponding to the vibrating frequency.

For example, at least one of the ultrasonic transducer elements may be one of a magnetostrictive ultrasonic transducer using the magnetostrictive effect of a magnetic body, a piezoelectric ultrasonic transducer using the piezoelectric effect of a piezoelectric material, and a capacitive micromachined ultrasonic transducer (cMUT) transmitting/receiving ultrasonic waves using vibration of hundreds or thousands of micromachined thin films. Further, at least one the ultrasonic transducer elements may be one of other kinds of transducer elements which may generate ultrasonic waves according to an electrical signal or generate an electrical signal according to ultrasonic waves.

The ultrasonic transmitter 122 causes the 2D ultrasonic transducer array 112 to transmit ultrasonic signals to a target site in an object. The ultrasonic transmitter 122 may include a transmission beamformer 120 and a transmission signal generator 130.

The transmission beamformer 120 forms a transmission beam and outputs the transmission beam to the transmission signal generator 130 according to a control signal from the controller 110. For example, transmission beamforming means that, when the transducer elements 114 transmit signals, the intensity of the signals is increased through superposition. The transmission beamformer 120 forms a transmission beam based on a time delay value of each of the ultrasonic transducer elements 114 of the 2D ultrasonic transducer array 112, calculated through the controller 110, and transmits the generated transmission beam to the transmission signal generator 130.

The transmission signal generator 130 generates an ultrasonic transmission signal using the transmission beam formed by the transmission beamformer 120. In more detail, the transmission signal generator 130 generates a transmission pulse which is transmitted to the object through the ultrasonic probe 102. For example, the transmission signal generator 130 may be an ultrasonic transmission pulse generator or a waveform generator generating an ultrasonic transmission pulse.

The transmission/reception switch unit 140 is switched to transmit the ultrasonic transmission pulse generated by the transmission signal generator 130 to the ultrasonic transducer array 112 in the ultrasonic probe 102, or to transmit ultrasonic echo signals received by the ultrasonic transducer array 112 to the ultrasonic receiver 142, according to a transmission control signal or a reception control signal transmitted from the controller 110.

The ultrasonic receiver 142 performs processing of ultrasonic echo signals received by the 2D ultrasonic transducer array 112. The ultrasonic receiver 142 may include a multiplexer 150, a reception signal generator 160, and a reception beamformer 170.

The multiplexer 150 is a combinational circuit which selects one of multiple input lines and connects the selected input line to a single output line. If ultrasonic echo signals received by the rows of the 2D ultrasonic transducer array 112 are defined as input signals of the multiplexer 150, the multiplexer 150 selects only the ultrasonic echo signal received by one row from the ultrasonic echo signals received by the rows of the 2D ultrasonic transducer array 112 and outputs the selected ultrasonic echo signal to the reception signal generator 160. The multiplexer 150 selects and outputs only a signal input from one row from signals input from the rows of the 2D ultrasonic transducer array 112 and may thus function as a row selector.

The reception signal generator 160 performs processing of ultrasonic echo signals received from the 2D ultrasonic transducer array 112. For example, the reception signal generator 160 may include a low noise amplifier (LNA) reducing noise of analog signals received from the ultrasonic transducer array 112 and a variable gain amplifier (VGA) controlling a gain value according to the input signals. The VGA may be a time gain compensator (TGC) compensating for a gain according to a distance from a focal point, but exemplary embodiments are not limited thereto.

The reception beamformer 170 performs beamforming based on ultrasonic signals, i.e., ultrasonic echo signals, of multiple channels transmitted from the ultrasonic transducer array 112. For example, reception beamforming means that, when the multiple ultrasound transducer elements 114 receive signals, the intensity of the signals is increased through superposition. That is, through reception beamforming, a proper ultrasonic image of the object may be acquired by focusing the reception signals input through the multiple channels. The reception beamformer 170 forms a reception focused beam based on time delay values of the respective ultrasonic transducer elements 114 of the 2D ultrasonic transducer array 112, and transmits the formed reception focused beam to the image processor 180.

The controller 110 controls the operations of the ultrasonic diagnostic apparatus 100. In more detail, the controller 110 generates designated control signals of the respective elements of the ultrasonic diagnostic apparatus 100, for example, the ultrasonic transmitter 122, the transmission/reception switch unit 140, the ultrasonic receiver 142, the image processor 180, and the display 108, shown in FIG. 10, thus controlling operation of the respective elements. The controller 110 calculates delay profiles of the ultrasonic transducer elements 114 of the 2D ultrasonic transducer array 112, calculates time delay values according to distance differences between the ultrasonic transducer elements 114 and a focal point of the object based on the calculated delay profiles, allows transmission and/or reception beams to be formed according to the calculated time delay values, and allows transmission and/or reception signals to be generated.

Further, the controller 110 may generate designated control commands regarding the respective elements of the ultrasonic diagnostic apparatus 100 according to predetermined settings or according to user instructions or commands input through the input unit 104, and thus controls the ultrasonic diagnostic device 100.

The image processor 180 generates a 3D ultrasonic image of the target site of the object based on the ultrasonic signals focused (beamformed) through the reception beamformer 170. The image processor 180 may include an image generator 181, a signal processor 182, a scan converter 183, a storage unit 184, and a volume image generator 185.

The image generator 181 generates a coherent 2D image or a 3D image data of the target site of the object based on the ultrasonic signals focused through the reception beamformer 170.

The signal processor 182 converts coherent image information formed by the image generator 181 into ultrasonic image information according to a diagnostic mode, such as a brightness mode (B-mode) or a Doppler mode (D-mode).

For example, if the B-mode is set as the diagnostic mode, the signal processor 182 performs processing, such as A/D conversion, and creates ultrasonic image information for B-mode images in real time. Further, if the D-mode is set as the diagnostic mode, the signal processor 182 extracts phase change information from the ultrasonic echo signals, calculates information of flow, for example, a blood flow, corresponding to each point of imaged cross-sections, such as speed, power, and dispersion, and creates ultrasonic image information for D-mode images in real time.

The scan converter 183 converts the converted ultrasonic image information input from the signal processor 182 or converted ultrasonic image information stored in the storage unit 184 into video signals for the display 108, i.e., performs format conversion into a screen format, and transmits the video signals to the volume image generator 185.

The storage unit 184 temporarily or non-temporarily stores the ultrasonic image information converted through the signal processor 182.

The volume image generator 185 performs volume rendering based on the video signals transmitted from the scan converter 183, generating a final resultant image by correcting rendered image information, and transmits the generated final resultant image to the display 108.

The input unit 104 allows a user to input a command regarding operation of the ultrasonic diagnostic device 100. The user may input an ultrasonic imaging start command, a diagnostic mode selection command to select one of an amplitude mode (A-mode), a brightness mode (B-mode), a color mode, a Doppler mode (D-mode), and a motion mode (M-mode), or set information of an ROI including the size and position of the ROI, information regarding rows to be used in reception of ultrasonic echo signals, as described above, and/or information regarding the number of ultrasonic transducer elements in each row to be used, as described above. For example, various units with which a user may input data, instructions or a command, for example, a keyboard, a mouse, a trackball, a tablet, or a touchscreen module, may be used as the input unit 104.

The display 108 displays a menu or guidance notice required for ultrasonic diagnosis and ultrasonic images acquired during an ultrasonic imaging. The display 108 may display an ultrasonic image of the target site of the object. The ultrasonic image displayed on the display 108 may be an A-mode ultrasonic image, a B-mode ultrasonic image, or a 3D stereoscopic ultrasonic image. For example, the display 108 may include a cathode ray tube (CRT) or a liquid crystal display (LCD).

FIG. 11 is a flowchart illustrating a control method of the ultrasonic diagnostic apparatus. The features described above with reference to FIGS. 1 to 10 are applicable here and will not be repeated.

In operation 210, the controller 110 acquires an ultrasonic imaging start command from the input unit 104, information regarding rows to be used in reception of ultrasonic echo signals, information regarding the number of ultrasonic transducer elements in each row to be used, and information of an ROI. The information of ROI includes the size and position of the ROI set in a reference sectional image. For example, the reference sectional image represents an image of a section vertical to a contact surface between the ultrasonic probe 102 and an object.

In operation 220, the controller 110 calculates delay profiles of the ultrasonic transducer elements 114 of the 2D ultrasonic transducer array 112. The controller 110 calculates time delay values according to distance differences between the plural ultrasonic transducer elements 114 of the 2D ultrasonic transducer array 112 and a focal point of the object based on the calculated delay profiles, and transmits the calculated time delay values to the transmission beamformer 120 within the ultrasonic probe 102. If defocused plane waves are transmitted, as exemplarily shown in FIGS. 3 and 7, calculation of delay profiles and time delay values is not required and thus, operation 220 may be omitted.

The controller 110 sends a control signal to the transmission beamformer 120 and the transmission signal generator 130 so that the 2D ultrasonic transducer array 112 transmits ultrasonic signals to the object (operation 230). For example, the controller 110 may control transmission of ultrasonic signals such that the ultrasonic signals may be transmitted using all of the ultrasonic transducer elements 114 of the 2D ultrasonic transducer array 112, as exemplarily shown in FIGS. 3 and 4, or be transmitted by sequentially using the ultrasonic transducer elements of one of the rows of the 2D ultrasonic transducer array 112, as exemplarily shown in FIGS. 5 to 8.

In operation 240, the controller 110 selects transducer elements desired to be activated in reception of ultrasonic echo signals, i.e., active reception transducer elements, from the ultrasonic transducer elements of the 2D ultrasonic transducer array 112 based on information regarding rows of the 2D ultrasonic transducer array 112 to be used in reception of ultrasonic echo signals and the number of ultrasonic transducer elements in each row to be used, received through the input unit 104. The controller 110 generates a control signal to activate the selected ultrasonic transducer elements and transmits the generated control signal to the multiplexer 150.

In operation 250, the ultrasonic echo signals are received by the selected active reception transducer elements. The received ultrasonic echo signals undergo processing in the reception signal generator 160 and are then transmitted to the reception beamformer 170.

In operation 260, the reception beamformer 170 performs reception beamforming in the transversal direction based on the received ultrasonic echo signals by sequentially using the ultrasonic transducer elements of one of the rows of the 2D ultrasonic transducer array 112. That is, the reception beamformer 170 performs dynamic reception focusing in the transversal direction using the ultrasonic echo signals received through the ultrasonic transducer elements 114 of each row of the 2D ultrasonic transducer array 112 and thus, acquires transversal planes P1 to PM corresponding to the respective rows of the 2D ultrasonic transducer array 112.

In operation 270, the reception beamformer 170 provides M ultrasonic transducer elements 114 of the elevation direction of one column and performs reception beamforming in the elevation direction by using the ultrasonic echo signals sequentially received in an order of the respective rows of the 2D ultrasonic transducer array 112. That is, the reception beamformer 170 forms a full aperture by sequentially storing the ultrasonic echo signals, sequentially received from the respective rows 116, 118, . . . , 119 of the 2D ultrasonic transducer array 112, in positions corresponding to the respective ultrasonic transducer elements of the elevation direction of one column, performs dynamic reception focusing or synthetic aperture focusing in the elevation direction using the full aperture, and thus, acquires a longitudinal plane $P_L$.

When the transmission/reception events are completed, the reception beamformer 170 performs 3D beamforming of the ROI using the transversal planes P1, P2, . . . , PM generated by performing dynamic reception focusing the ultrasonic echo signals received through the ultrasonic transducer elements of the respective rows 116, 118, ..., 119 of the 2D ultrasonic transducer array 112 and the longitudinal plane $P_L$ generated by performing dynamic reception focusing or synthetic aperture focusing in the elevation direction based on the ultrasonic echo signals in the elevation direction (the full aperture in the elevation direction), formed by using the ultrasonic echo signals sequentially received according to the respective rows. The reception beamformer 170 transmits 3D beamformed ultrasonic signals to the image generator 181.

In operation 280, the image generator 181 generates a coherent 3D image of the ROI based on the ultrasonic signals focused (beamformed) through the reception beamformer 170. The image generator 181 transmits the generated 3D image to the signal.

In operation 290, the signal processor 182 performs image processing of the 3D image information transmitted from the image generator 181, and the volume image generator 185 performs volume rendering based on the 3D image information upon which image processing and format conversion have been performed. The volume image generator 185 corrects the rendered image information and thus generates a final resultant image, and transmits the final resultant image to the display 108.

The 3D ultrasonic image (volume-rendered image) of the ROI generated through the volume image generator 185 is displayed by the display 108 according to a control signal from the controller 110.

In an exemplary embodiment, ultrasonic signals are transmitted by using all of the ultrasonic transducer elements 114 of the 2D ultrasonic transducer array 112 or by using the ultrasonic transducer elements 114 of one or more rows of the 2D ultrasonic transducer array 112, and ultrasonic echo signals are received by using one or more ultrasonic transducer elements 114 of one of the rows of the 2D ultrasonic transducer array 112. Therefore, an exemplary embodiment using the 2D ultrasonic transducer array 112 maintains the same number of system channels as when 1D ultrasonic transducer array is used and may thus maximize resolution of an ultrasonic image during volume beamforming without increase in the number of connection cables between the ultrasonic probe 102 and the system (main body).

The above-described exemplary embodiments illustrate the method in which the ultrasonic transducer elements and the system channels are connected so that ultrasonic signals may be transmitted from all of the ultrasonic transducer elements 114 of the 2D ultrasonic transducer array 112 or the ultrasonic transducer elements 114 of one or more rows of the rows of the 2D ultrasonic transducer array 112, and reception of ultrasonic echo signals is controlled by switching the rows of the 2D ultrasonic transducer array 112 one by one, so as to reduce the number of reception channels and to improve resolution of a volume image. However, in order to increase a volume rate, transmission of ultrasonic signals may be controlled by switching the rows of the 2D ultrasonic transducer array 112 one by one, and ultrasonic echo signals may be received using all of the ultrasonic transducer elements 114 of the 2D ultrasonic transducer array 112 or the ultrasonic transducer elements 114 of one or more rows of the 2D ultrasonic transducer array 112.

As apparent from the above description, an ultrasonic diagnostic apparatus and a control method thereof, in accordance with an exemplary embodiment, generates a 3D ultrasonic image using a 2D ultrasonic transducer array and may improve resolution and scanning speed of the 3D ultrasonic image.

Further, the ultrasonic diagnostic apparatus and the control method thereof, in generation of a 3D ultrasonic image using a 2D ultrasonic transducer array, may generate a 3D ultrasonic image of an object even with a compact-size system, i.e., a system having low complexity.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasonic diagnostic apparatus comprising:
   an ultrasonic transducer array in which ultrasonic transducer elements are two dimensionally arranged in rows which extend in a lengthwise direction of the ultrasonic transducer array and columns which extend in an elevation direction perpendicular to the lengthwise direction; and
   a controller configured to control a transmission of ultrasonic signals, by controlling the ultrasonic transducer elements to transmit the ultrasonic signals in transmission events, and to control a reception of ultrasonic echo signals in reception events by controlling the ultrasonic transducer elements arranged in the rows to sequentially receive ultrasonic echo signals by shifting the rows in the elevation direction,
   wherein the controller is further configured to:
   (a) control, for a corresponding transmission event among the transmission events, an aperture formed by the ultrasonic transducer elements to transmit the ultrasonic signals,
   (b) based on the corresponding transmission event, control one reception event, among the reception events, the controlling the one reception event comprising controlling the ultrasonic transducer elements in one row, among the rows, to receive the ultrasonic echo signals, while sequentially shifting, in the elevation direction, a position of the one row in which the ultrasonic transducer elements are controlled to receive the ultrasonic echo signals until all of the rows in the elevation direction receive the ultrasonic echo signals corresponding to the ultrasonic signals transmitted by the aperture in the corresponding transmission event, and
   (c) repeat steps (a) and (b) until all of the transmission events of transmitting the ultrasonic signals by the ultrasonic transducer elements are completed.

2. The ultrasonic diagnostic apparatus according to claim 1, wherein the controller is further configured to control all of the ultrasonic transducer elements to transmit defocused plane waves, in each of the transmission events.

3. The ultrasonic diagnostic apparatus according to claim 1, wherein the controller is further configured to control the ultrasonic transducer elements arranged in one of the rows of the ultrasonic transducer array to sequentially transmit defocused plane waves, in each of the transmission events.

4. The ultrasonic diagnostic apparatus according to claim 1, wherein the controller is further configured to control all of the ultrasonic transducer elements of the ultrasonic transducer array to transmit ultrasonic waves in each of the transmission events, and to perform fixed focusing of the ultrasonic waves.

5. The ultrasonic diagnostic apparatus according to claim 1, wherein the controller is further configured to control the ultrasonic transducer elements arranged in one of the rows of the ultrasonic transducer array to sequentially transmit ultrasonic waves in each of the transmission events, and to perform fixed focusing of the ultrasonic waves.

6. The ultrasonic diagnostic apparatus according to claim 1, wherein the controller is further configured to control the rows to be sequentially switched one by one to receive the ultrasonic echo signals while shifting the position of the one row in the elevation direction, in each of the reception events.

7. The ultrasonic diagnostic apparatus according to claim 1, wherein the controller is further configured to form a table including virtual columns in correspondence to the columns of the ultrasonic transducer elements in the ultrasonic transducer array, and to generate ultrasonic data for reception beamforming in the elevation direction by sequentially storing the received ultrasonic echo signals, at positions in the virtual columns in correspondence to positions of the ultrasonic transducer elements arranged in the columns of the ultrasonic transducer array.

8. The ultrasonic diagnostic apparatus according to claim 7, wherein the controller is further configured to control a dynamic reception focusing or a synthetic aperture focusing in the elevation direction using the generated ultrasonic data for the reception beamforming in the elevation direction.

9. The ultrasonic diagnostic apparatus according to claim 8, wherein the controller is further configured to control an execution of a volume beamforming by using the ultrasonic echo signals sequentially received from the rows of the ultrasonic transducer elements and the generated ultrasonic data for the reception beamforming in the elevation direction.

10. A control method of an ultrasonic diagnostic apparatus, the control method comprising:
controlling a transmission of ultrasonic signals by ultrasonic transducer elements in transmission events, the ultrasonic transducer elements being two-dimensionally arranged in an ultrasonic transducer array in rows which extend in a lengthwise direction of the ultrasonic transducer array and columns which extend in an elevation direction perpendicular to the lengthwise direction; and
controlling a reception of ultrasonic echo signals in reception events, to sequentially receive the ultrasonic echo signals in the elevation direction by the ultrasonic transducer elements arranged in the rows,
wherein the control method further comprises:
(a) controlling, for a corresponding transmission event among the transmission events, an aperture formed by the ultrasonic transducer elements to transmit the ultrasonic signals,
(b) based on the corresponding transmission event, controlling one reception event, among the reception events, the controlling the one reception event comprising controlling the ultrasonic transducer elements in one row, among the rows, to receive the ultrasonic echo signals, while sequentially shifting, in the elevation direction, a position of the one row in which the ultrasonic transducer elements are controlled to receive the ultrasonic echo signals until all of the rows in the elevation direction receive the ultrasonic echo signals corresponding to the ultrasonic signals transmitted by the aperture in the corresponding transmission event, and
(c) repeating steps (a) and (b) until all of the transmission events of transmitting the ultrasonic signals by the ultrasonic transducer elements are completed.

11. The control method according to claim 10, wherein the controlling the transmission comprises:
controlling all of the ultrasonic transducer elements to transmit defocused plane waves.

12. The control method according to claim 10, wherein the controlling the transmission comprises:
controlling the ultrasonic transducer elements arranged in one of the rows of the ultrasonic transducer array to sequentially transmit defocused plane waves.

13. The control method according to claim 10, wherein the controlling the transmission comprises:
controlling all of the ultrasonic transducer elements to transmit ultrasonic waves and perform fixed focusing of the ultrasonic waves.

14. The control method according to claim 10, wherein the controlling the transmission comprises:
controlling the ultrasonic transducer elements arranged in one of the rows of the ultrasonic transducer array to sequentially transmit ultrasonic waves and perform fixed focusing of the ultrasonic waves.

15. The control method according to claim 10, wherein the controlling the reception further comprises:
sequentially switching the rows of the ultrasonic transducer array one by one; and
receiving the ultrasonic echo signals while shifting the position of the one row in the elevation direction.

16. The control method according to claim 10, wherein the controlling the reception further comprises forming a table including virtual columns in correspondence to the columns of the ultrasonic transducer elements in the ultrasonic transducer array, and
the control method further comprises generating a volume image,
wherein the generating the volume image comprises generating ultrasonic data for reception beamforming in the elevation direction by sequentially storing the received ultrasonic echo signals at positions in the virtual columns in correspondence to positions of the ultrasonic transducer elements arranged in the columns in the ultrasonic transducer array.

17. The control method according to claim 16, wherein the generating the volume image further comprises:
performing a dynamic reception focusing or a synthetic aperture focusing in the elevation direction using the generated ultrasonic data for the reception beamforming in the elevation direction.

18. The control method according to claim 17, wherein the generating the volume image further comprises:
performing a volume beamforming by using the ultrasonic echo signals sequentially received from the rows of the ultrasonic transducer elements and the generated ultrasonic data for the reception beamforming in the elevation direction.

19. An ultrasonic apparatus comprising:
an ultrasonic probe comprising ultrasonic transducer elements which are two-dimensionally arranged in an array comprising rows which extend in a lengthwise direction of the array and columns which extend in an elevation direction perpendicular to the lengthwise direction; and
a processor configured to perform steps of:
activating all or some of the ultrasonic transducer elements arranged in the rows, to transmit ultrasonic signals to an object in transmission events,
controlling scanning by all or some of the ultrasonic transducer elements arranged in the rows to receive ultrasonic echo signals reflected by the object in reception events, while activating the rows of the ultrasonic transducer elements one by one in a sequential order of the rows in the elevation direction, storing the ultrasonic echo signals while performing the scanning of the rows, and generating a three-dimensional (3D) ultrasonic image based on the ultrasonic echo signals sequentially received from each of the rows in the elevation direction, wherein the processor is further configured to perform steps of:

(a) controlling, for a corresponding transmission event among the transmission events, an aperture formed by the ultrasonic transducer elements to transmit the ultrasonic signals, (b) based on the corresponding transmission event, controlling one reception event, among the reception events, the controlling the one reception event comprising controlling the ultrasonic transducer elements in one row, among the rows, to receive the ultrasonic echo signals, while sequentially shifting, in the elevation direction, a position of the one row in which the ultrasonic transducer elements are controlled to receive the ultrasonic echo signals until all of the rows in the elevation direction receive the ultrasonic echo signals corresponding to the ultrasonic signals transmitted by the aperture in the corresponding transmission event, and (c) repeating steps (a) and (b) until all of the transmission events of transmitting the ultrasonic signals by the ultrasonic transducer elements are completed.

20. The ultrasonic apparatus of claim 19, wherein the storing comprises:

storing the ultrasonic echo signals received by scanning the rows in virtual columns of a table, the virtual columns being arranged in correspondence to the columns of the ultrasonic transducer elements in the array, wherein the received ultrasonic echo signals are stored at positions in the virtual columns in correspondence to column positions of the ultrasonic transducer elements in the array.

21. The ultrasonic apparatus of claim 20, wherein the generating the 3D ultrasonic image comprises:

generating ultrasonic data in the elevation direction from the ultrasonic echo signals stored in the virtual columns;

generating the 3D ultrasonic image by using the generated ultrasonic data in the elevation direction and the ultrasonic echo signals stored while performing the scanning of the rows; and displaying the 3D image on a display.

* * * * *